United States Patent [19]
Liao et al.

[11] Patent Number: 6,153,378
[45] Date of Patent: *Nov. 28, 2000

[54] DIAGNOSIS OF, AND VACCINATION AGAINST, A POSITIVE STRANDED RNA VIRUS USING AN ISOLATED, UNPROCESSED POLYPEPTIDE ENCODED BY A SUBSTANTIALLY COMPLETE GENOME OF SUCH VIRUS

[75] Inventors: Jaw-Ching Liao; Cheng-Nan Wang, both of Taipei, Taiwan

[73] Assignee: Bionova Corporation, San Francisco, Calif.

[*] Notice: This patent is subject to a terminal disclaimer.

[21] Appl. No.: 08/454,928

[22] Filed: May 31, 1995

Related U.S. Application Data

[63] Continuation-in-part of application No. 07/962,989, Oct. 16, 1992, abandoned, and a continuation-in-part of application No. 08/143,579, Oct. 26, 1993, Pat. No. 5,625,034, which is a division of application No. 07/963,483, Oct. 16, 1992, abandoned.

[51] Int. Cl.$^7$ ............................. C12Q 1/70; A61K 39/29
[52] U.S. Cl. ............................. 435/5; 435/7.1; 435/69.3; 435/471; 435/810; 435/948; 424/189.1; 424/192.1; 424/204.1
[58] Field of Search ............................. 435/5, 7.1, 69.3, 435/471, 810, 948; 424/189.1, 192.1, 204.1

[56] References Cited

U.S. PATENT DOCUMENTS

| | | | |
|---|---|---|---|
| 5,106,726 | 4/1992 | Wang | 435/5 |
| 5,350,671 | 9/1994 | Houghton et al. | 435/5 |
| 5,645,983 | 7/1997 | Liano et al. | 435/5 |

FOREIGN PATENT DOCUMENTS

| | | | |
|---|---|---|---|
| 0318216 | 5/1989 | European Pat. Off. | |
| 318 216 | 5/1989 | European Pat. Off. | |
| 0 450 931 A1 | 4/1990 | European Pat. Off. | |
| 0388232 | 9/1990 | European Pat. Off. | |
| 388 232 | 9/1990 | European Pat. Off. | |
| 442 394 A2 | 8/1991 | European Pat. Off. | |
| 450 931 A1 | 10/1991 | European Pat. Off. | |
| 463 848 A2 | 1/1992 | European Pat. Off. | |
| 518 313 A2 | 12/1992 | European Pat. Off. | |
| 593 290 A2 | 4/1994 | European Pat. Off. | C12N 15/51 |
| 593 291 A2 | 4/1994 | European Pat. Off. | C12N 15/51 |
| 2239245 | 6/1991 | United Kingdom | |
| WO 91/15516 | 10/1991 | WIPO | C07K 15/00 |
| 9203458 | 3/1992 | WIPO | |
| WO 92/11370 | 7/1992 | WIPO | C12N 15/51 |
| WO 93/17110 | 9/1993 | WIPO | |
| WO 94/25486 | 11/1994 | WIPO | |

OTHER PUBLICATIONS

Hsu et al., "Characterization of Hepatitis C Virus Structural Proteins with a Recombinant Baculovirus Expression System," *Hepatology* 17(5): 763–771, 1993.
Matsuura et al., "Glycosylated Envelope Protein of Hepatitis C Virus Expressed in Animal Cells," in *Vaccines 92*, Cold Spring Harbor Laboratory, NY, 1992, pp. 309–314.
Chau et al., "IgM–antibody response to hepatitis C virus antigens in acute and chronic post–transfusion non–A, non–B hepatitis," *Journal of Virological Methods 35:* 343–352, 1991.
Chen et al., "The Taiwanese Hepatitis C Virus Genome: Sequence Determination and Mapping the 5' Termini of Viral Genomic and Antigenomic RNA," *Virology 188:* 102–113, 1992.
Chiba et al., "Serodiagnosis of hepatitis C virus (HCV) infection with an HCV core protein molecularly expressed by a recombinant baculovirus," *Proc. Natl. Acad. Sci. USA 88:* 4641–4645, 1991.
Ching et al., "Interaction of immune sera with synthetic peptides corresponding to the structural protein region of hepatitis C virus," *Proc. Natl. Acad. Sci. USA 89:* 3190–3194, 1992.
Chou et al., "Empirical Predictions of Protein Conformation," *Ann. Rev. Biochem 47:* 251–276, 1978.
Clark et al., "Enzyme–Linked Immunosorbent Assay (Elisa): Theoretical and Practical Aspects," *Enzyme Immunoassay*, pp. 167–179, 1980.
Clemens et al., "IgM Antibody Response in Acute Hepatitis C Viral Infection," *Blood* 79(1): 169–172, 1992.
Harada et al., "Expression of Processed Core Protein of Hepatitis C Virus in Mammalian Cells," *Journal of Virology* 65(6): 3015–3021, 1991.
Hijikata et al., "Gene Mapping of the putative structural region of the hepatitis C virus genome by in vitro processing analysis," *Proc. Natl. Acad. Sci. USA 88:* 5547–5551, 1991.
Inchauspe et al., "Genome structure of the human prototype strain H of hepatitis C virus: Comparison with American and Japanese isolates," *Proc. Natl. Acad. Sci. USA 88:* 10292–10296, 1991.
Inchauspe et al., "Use of Conserved Sequences from Hepatitis C Virus for the Detection of Viral RNA in Infected Sera by Polymerase Chain Reaction," *Hepatology* 14(1): 595–600, 1991.

(List continued on next page.)

*Primary Examiner*—Marianne P. Allen
*Assistant Examiner*—Mary K Zeman
*Attorney, Agent, or Firm*—Seed Intellectual Property Law Group PLLC

[57] ABSTRACT

The unprocessed polyprotein initially translated from the genome of a positive-stranded RNA virus contains epitopic configurations that are not retained in the processed proteins. The structural protein region, in particular, loses an epitopic configuration upon processing at the cleavage site between the genomic region encoding the core protein and the genomic region encoding the protein adjacent the core protein, such as the envelope protein in HCV. Compositions, methods and assays relating to the diagnosis and detection of the presence of the positive-stranded RNA virus, or antibodies to the positive-stranded RNA virus, in a sample. Compositions and methods for the induction of immune responses in, and vaccination of, an animal. Combination of the unprocessed core region with a non-structural protein (such as an NS5 or an unprocessed NS3-NS4 fusion from HCV).

14 Claims, 6 Drawing Sheets-

OTHER PUBLICATIONS

Kato et al., "Molecular cloning of the human hepatitis C virus genome from Japanese patients with non–A, non–B hepatitis," *Proc. Natl. Acad. Sci. USA 87:* 9524–9528, 1990.

Kato et al, "A Structural Protein Encoded by the 5' Region of the Hepatitis C Virus Genome Efficiently Detects Viral Infection," *Japanese Journal of Cancer Research 81*(11): 1092–1094, 1990.

Muller et al., "Genetic Variability of German Hepatitis C Virus Isolates," *Journal of Medical Virology 40:* 291–306, 1993.

Munekata et al., "Epitope–mapping of hepatitis C virus constituting protein," *Peptide Chemistry* (ed. Shimonisihi, Y., Protein Research Foundation, Osaka), pp. 211–214, 1991.

Muraiso et al., "A structural protein of hepatitis C virus expressed in *E. coli* facilitates accurate detection of hepatitis C virus," *Biochem. Biophys. Research Communications 172*(2): 511–516, 1990.

Nasoff et al., "Identification of an immunodominant epitope within the capsid of hepatitis C virus," *Proc. Natl. Acad. Sci. USA 88:* 5462–5466, 1991.

Okamoto et al., "Full–Length Sequence of a Hepatitis C Virus Genome Having Poor Homology to Reported Isolates: Comparative Study of Four Distinct Genotypes," *Virology 188:* 331–341, 1992.

Okamoto et al., "Antibodies against synthetic oligopeptides deduced from the putative core gene for the diagnosis of hepatitis C virus infection," *Hepatology 15:* 180–186, 1992.

Sallberg et al., "Immune response to a single peptide containing an immunodominant region of hepatitis C virus core protein: the isotypes and the recognition site," *Immunology Letters 33:* 27–34, 1992.

Sallberg et al., "Immunodominant Regions within the Hepatitis C Virus Core and Putative Matrix Proteins," *Journal of Clinical Micro. 30*(8): 1989–1994, 1992.

Takamizawa et al., "Structure and Organization of the Hepatitis C Virus Genome Isolated from Human Carriers," *Journal of Virology 65*(3): 1105–1113, 1991.

Shitari et al., J. Clin. Microbio. 28(9): 2022–2029, 1990.

Jemmerson, Immunological Recognition of Peptides in Medicine and Biology, pp. 213–225, 1995.

Rudinger et al. Peptide Hormones, 1976.

Harada et al. J. Virol. 65(6): 3015–3021, 1991.

Hijikata et al. PNAS (USA): 88: 5547–5551, 1991.

Nucleotide Sequence ID 7

| | |
|---|---|
| 5'-ATGAGCACAAATCCTAAACCTCAAAGAAAAACCAAACGTAACACCAACCGCCGCCCACAG | 60 |
| GACGTCAAGTTCCCGGGCGGTGGTCAGATCGTTGGTGGAGTTTACCTGTTGCCGCGCAGG | 120 |
| GGCCCCAGGTTGGGTGTGCGCGCGACTAGGAAGACTTCCGAGCGGTCGCAACCTCGTGGA | 180 |
| AGGCGACAACCTATCCCCAAGGCTCGCCGGCCCGAGGGCAGGACCTGGGCTCAGCCGGGG | 240 |
| TACCCTTGGCCCCTCTATGGCAATGAGGGTCTGGGGTGGGCAGGATGGCTCCTGTCACCC | 300 |
| CGAGGCTCTCGGCCTAGTTGGGGCCCCACGGACCCCCGGCGTAGGTCGCGTAATCTGGGT | 360 |
| AAGGTCATCGATACCCTCACAGGTGGCTTCGCCGACCTCATGGGGTACATTCCGCTCGTC | 420 |
| AGCGCCCCACTAGGAGGCGCTGCCAGGGCCCTGGGCCATGGCGTCCGGGTTCTGGAGGAC | 480 |
| GGCGTGAACTATGCAACAGGGAATCTGCCCGGTTGCTCTTTCTCTATCTTCCTCTTAGCT | 540 |
| TTGCTGTCTTGTTTGACCATCCCAGCTTCCGCTTACGAGGTGCGCAACGTGTCCGGGATA | 600 |
| TACCATGTTACGAACGATTGCTCCAACTCAAGTATCGTGTATGAGGCAGCGGACATGATC | 660 |
| ATGCACACC-3' | 669 |

*Fig. 1A*

Amino Acid Sequence ID 8

| | |
|---|---|
| NH2-MetSerThrAsnProLysProGlnArgLysThrLysArgAsnThr | 15 |
| AsnArgArgProGlnAspValLysPheProGlyGlyGlyGlnIle | 30 |
| ValGlyGlyValTyrLeuLeuProArgArgGlyProArgLeuGly | 45 |
| ValArgAlaThrArgLysThrSerGluArgSerGlnProArgGly | 60 |
| ArgArgGlnProIleProLysAlaArgArgProGluGlyArgThr | 75 |
| TrpAlaGlnProGlyTyrProTrpProLeuTyrGlyAsnGluGly | 90 |
| LeuGlyTrpAlaGlyTrpLeuLeuSerProArgGlySerArgPro | 105 |
| SerTrpGlyProThrAspProArgArgArgSerArgAsnLeuGly | 120 |
| LysValIleAspThrLeuThrGlyGlyPheAlaAspLeuMetGly | 135 |
| TyrIleProLeuValSerAlaProLeuGlyGlyAlaAlaArgAla | 150 |
| LeuGlyHisGlyValArgValLeuGluAspGlyValAsnTyrAla | 165 |
| ThrGlyAsnLeuProGlyCysSerPheSerIlePheLeuLeuAla | 180 |
| LeuLeuSerCysLeuThrIleProAlaSerAlaTyrGluValArg | 195 |
| AsnValSerGlyIleTyrHisValThrAsnAspCysSerAsnSer | 210 |
| SerIleValTyrGluAlaAlaAspMetIleMetHisThr-COOH | 223 |

*Fig. 1B*

Nucleotide Sequence ID 9

| | |
|---|---:|
| 5'-GTGGAGGATGAGAGGGAAATATCCGTTGAGGCGGAGATCCTGCGTTTTTCCAGGAAATTC | 60 |
| CCCCGGGCGATACCCATATGGGCCCGCCCGGATTACAATCCACCACTGATAGAGTCCTGG | 120 |
| AAGGACCCGGACTATGTCCCCCCGGTGGTACACGGGTGCCCATTGCCACCTGCCAAGATC | 180 |
| CCTCCAATACCACCTCCACGGAGGAAGAAGACGGTTGTCCTGACAGAGTCCGTCTATACT | 240 |
| TCTGCCCTGGCGGACGTTGCTACAAAGACCTTCGGCAGCTCCGAGTCTACGCCCGTCGAC | 300 |
| AGCGGCACAGCGACTGGCCTCCCGATCAACCTTCTGACGACGGCGACAAAGGGATCCGAC | 360 |
| GTTGAGTCGTACTCCTCCATGCCCCCCCTCGAGGGAGAGCCAGGCGACCCCGATCTCAGC | 420 |
| GACGGGTCTTGGTCTACTGTGAGCGTGGAGGCTAGTGAGGACGTTGTCTGCTGCTCGATG | 480 |
| TCCTACACATGGACAGGCGCTTTAATCACGCCATGCGCTGCGGAGGAGAGCAAACTGCCC | 540 |
| ATCAATGCGTTGAGCTTCTCTTTGTTGCGTCACCACAATATGGTCTACGCCACAACATCC | 600 |
| CGCAGCGCAGACCAGCCGCAGAAAAAGGTCACCTTTGACAGACTGCAAGTCCTGGACGAC | 660 |
| CACTACCGGGACGTACTCAAGGAGATGAAGGCGAAGGCGTCTACAGTTAAGGCTAAACTT | 720 |
| CTATCCGTAGAAGAGGCCTGTAACGTGACGCCCCCACATTCGGCCAAATCCAAATTTGGC | 780 |
| TACGGGGCGAAGGACGTCCGG-3' | 801 |

*Fig. 3A*

Amino Acid Sequence ID 10

| | |
|---|---|
| NH2-ValGluAspGluArgGluIleSerValGluAlaGluIleLeuArg | 15 |
| PheSerArgLysPheProArgAlaIleProIleTrpAlaArgPro | 30 |
| AspTyrAsnProProLeuIleGluSerTrpLysAspProAspTyr | 45 |
| ValProProValValHisGlyCysProLeuProProAlaLysIle | 60 |
| ProProIleProProProArgArgLysLysThrValValLeuThr | 75 |
| GluSerValTyrThrSerAlaLeuAlaAspValAlaThrLysThr | 90 |
| PheGlySerSerGluSerThrProValAspSerGlyThrAlaThr | 105 |
| GlyLeuProIleAsnLeuLeuThrThrAlaThrLysGlySerAsp | 120 |
| ValGluSerTyrSerSerMetProProLeuGluGlyGluProGly | 135 |
| AspProAspLeuSerAspGlySerTrpSerThrValSerValGlu | 150 |
| AlaSerGluAspValValCysCysSerMetSerTyrThrTrpThr | 165 |
| GlyAlaLeuIleThrProCysAlaAlaGluGluSerLysLeuPro | 180 |
| IleAsnAlaLeuSerPheSerLeuLeuArgHisHisAsnMetVal | 195 |
| TyrAlaThrThrSerArgSerAlaAspGlnProGlnLysLysVal | 210 |
| ThrPheAspArgLeuGlnValLeuAspAspHisTyrArgAspVal | 225 |
| LeuLysGluMetLysAlaLysAlaSerThrValLysAlaLysLeu | 240 |
| LeuSerValGluGluAlaCysAsnValThrProProHisSerAla | 255 |
| LysSerLysPheGlyTyrGlyAlaLysAspValArg-COOH | 267 |

Fig. 3B

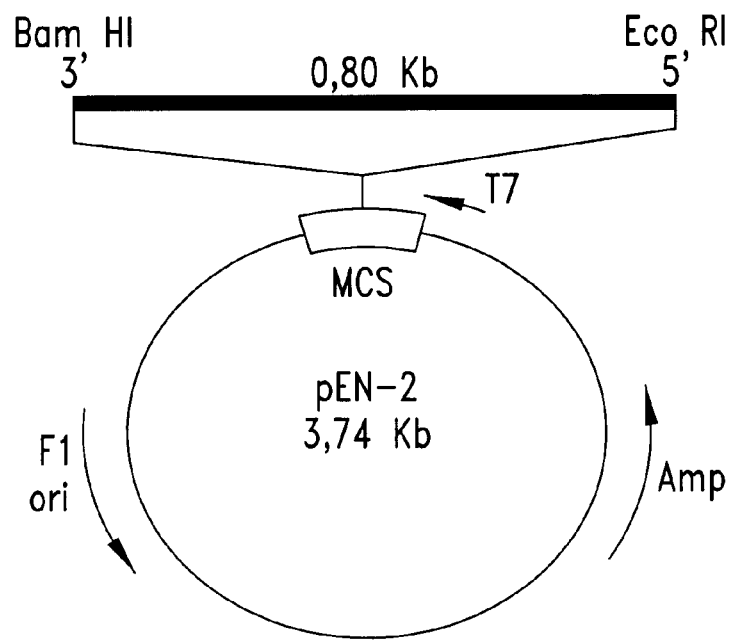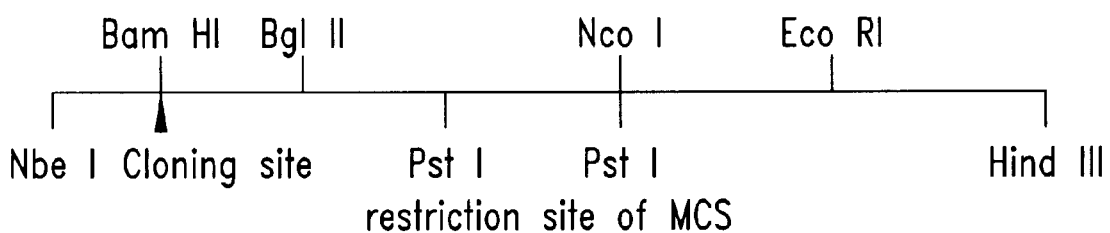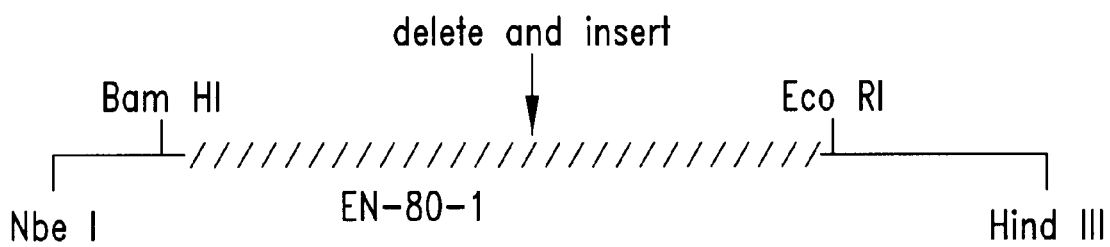
Fig. 4

DIAGNOSIS OF, AND VACCINATION AGAINST, A POSITIVE STRANDED RNA VIRUS USING AN ISOLATED, UNPROCESSED POLYPEPTIDE ENCODED BY A SUBSTANTIALLY COMPLETE GENOME OF SUCH VIRUS

CROSS-REFERENCE TO RELATED APPLICATIONS

This application is a continuation-in-part application of U.S. patent application Ser. No. 07/962,989, filed Oct. 16, 1992, abandoned, and this application is a continuation-in-part of U.S. patent application Ser. No. 08/143,579, filed Oct. 26, 1993 now U.S. Pat. No. 5,625,034, issued Apr. 29, 1997, which application is a divisional application of U.S. patent application Ser. No. 07/963,483, filed Oct. 16, 1992, abandoned.

TECHNICAL FIELD

The present invention relates generally to methods and compositions for the highly specific, highly sensitive diagnosis of a positive-stranded RNA virus. The methods and compositions are also suitable for the elicitation of an immune response in an animal, and for the vaccination of an animal, against a positive-stranded RNA virus.

BACKGROUND OF THE INVENTION

Acquired immune deficiency syndrome (AIDS) is caused by a group of retroviruses known as HIV (Barre-Sinoussi et al., *Science* 220:868–871, 1983; Gallo et al., Science 224:500–503, 1984; Coffin et al., *Science* 232:697, 1986). The first member of the group has been designated HIV-1 and is responsible for a majority of cases of AIDS worldwide. It is distinguished from HIV-2, an isolate discovered from WAf (Clavel et al., *Science* 233:343–346, 1986). Although HIV-2, like HIV-1, produces symptoms of immune deficiency in man, it is also genetically distinct from HIV (Guyader et al., *Nature* 326:662–669, 1987).

The genomes of the HIV isolates, like those of other retroviruses, include three basic genes: gag, pol and env (Weiss et al., Cold Spring Harbor Laboratory, Cold Spring Harbor, N.Y., 1985). In addition, the genomes contain several other genes whose products play important roles in the regulation of viral gene expression (Dayton et al., Cell 44:941 . 947, 1986; Fisher et al., *Nature* 320:367–371, 1986; Sodroski et al., *Nature* 321:412–417, 1986).

HIV-1 is typically transmitted by sexual contact, by exposure to blood or certain blood products, or by an infected mother to her fetus or child (Piot et al., *Science* 239:573–579, 1988). The first examples of transfusion-associated HIV-2 infection have been disclosed (Courouce et al., *AIDS* 2:261–265, 1988). Therefore, the demand for sensitive and specific methods for detecting HIV in contaminated blood or blood products is significant.

EIAs, based on whole virus or viral lysate, have been developed for the detection of HIV. However, it has been found that the EIAs have unacceptable, non-specific reaction with specimens from individuals with non-HIV conditions such as autoimmune diseases, a history of multiple pregnancies, anti-BLA, EBV infections or hypergammaglobulinemia.

In order to avoid such non-specific reactions and in an attempt to detect anti-HIV-1 and/or anti-HIV-2 in samples, an ELISA has been developed and commercialized by Abbott Laboratories for serological diagnosis of HIV infection using the HIV-I core and HIV-1 envelope and HIV-2 envelope proteins. However, this ELISA has not provided the highly specific, highly sensitive detection needed for superior protection of the blood supply, or for early diagnosis of HIV in a patient.

Thus, in order to provide superior protection of the blood supply, and in order to provide superior diagnosis of HIV in a patient, there has gone unmet a need for products and methods capable of highly specific, highly sensitive detection of HIV. There has also gone unmet a need for products and methods capable of eliciting an immune response to HIV, especially an immunoprotective immune response to HIV. The present invention provides these and other related advantages.

In addition to the problems associated with HIV, other positive-stranded RNA viruses also pose significant health risks throughout the world. One example of such a positive-stranded RNA virus is the Hepatitis C virus (HCV). HCV is distinguishable from other forms of viral-associated liver diseases caused by known hepatitis viruses such as hepatitis A virus (HAV) and hepatitis B virus (HBV). Like HIV, HCV is often transferred via blood transfusion; post-transfusion hepatitis (PTH) occurs in approximately 10% of transfusion patients, and HCV (i.e., Non-A, Non-B hepatitis (NANBH)) accounts for up to 90% of these cases. A major problem arising from this disease is the frequent progression to chronic liver damage (25–55%). Therefore, the demand for sensitive, specific methods for detecting HCV in contaminated blood or blood products is significant.

The hepatitis C virus (HCV) was first identified by molecular cloning and characterization of its RNA genome by Choo et al. (*Science* 244:359–362, 1989). A specific assay using an HCV antigen designated C100-3 was then created, using recombinant DNA methods in yeast. The assay detects an antibody against HCV (*Science* 244:362–364). A detailed disclosure of the genome of HCV, and some cDNA sequences and polypeptides derived therefrom, as well as methodologies relating to such subject matter, is provided in EP 0 318 216 A1 in the name of Chiron Corporation. In particular, this disclosure provides a synthesized polypeptide, C100-3, containing 363 virally-encoded amino acids that can be used for the detection of one type of HCV antibody. Presently, kits for detecting HCV antibodies on the basis of the C100-3 antigen have been commercialized by Abbott Laboratories.

As suggested in EP 0 318 216 A1, HCV may be a flavivirus or flavi-like virus. With respect to general morphology, a flavivirus contains a central nucleocapsid surrounded by a lipid bilayer. It is believed that hepatitis C virus protein is composed of structural proteins including a nucleocapsid (core) protein (C), two glycosylated envelope proteins (E1, E2) and several nonstructural proteins (NS-5). It has been confirmed that C100-3 disclosed by Choo et al. is a protein encoded by part of nonstructural regions 3–4 of the HCV genome. It has been found that anti-C100-3 antibody is not detected in all post-transfision NANBH cases. The failure to detect the anti-C100-3 antibody is possibly due to hypermutation of the nucleotide sequence in C100-3 region.

In addition to the work with the nonstructural C100-3 antigen, an enzyme-linked immunosorbent assay (ELISA) has been developed for serological diagnosis of hepatitis C virus (HCV) infection using the HCV core protein (p22). The core protein was synthesized by a recombinant baculovirus, as reported in Chiba et al. (*Proc. Natl. Acad. Sci. USA* 88:4641–4645, 1991). Thus, the assay of Chiba, et al. used a nonglycosylated 22-kDa nucleocapsid (core) protein, in an effort to establish an antibody-based, specific, sensitive method for diagnosing HCV infection. However, this core protein-based assay failed to detect a significant number of cases of HCV infection, even when relatively large sample volumes were available.

Thus, as with other positive-stranded RNA viruses, there has gone unmet a need for products and methods capable of highly specific, highly sensitive detection of HCV. There has also gone unmet, as with other positive-stranded RNA viruses, a need for products and methods capable of eliciting an immune response to HCV, especially an immunoprotective immune response to HCV. The present invention provides these and other related advantages.

SUMMARY OF THE INVENTION

The present invention is directed toward the concept that unprocessed entire polypeptide(s) (e.g., a polyprotein) or unprocessed partial polypeptide(s) in the structural region and proteins from the non-structural region of positive-stranded ((+)-stranded) RNA viruses can provide a superior antigenicity and therefore an improved detection and diagnosis of a positive-stranded RNA virus in a sample. The present invention also provides improved immunoactivation, including an improved immunoprotective response from an animal.

Accordingly, in a first aspect the present invention provides positive-stranded RNA virus-derived compositions comprising an isolated, substantially complete, unprocessed polyprotein from a positive-stranded RNA virus. In alternative aspect, the present invention provides positive-stranded RNA virus-derived compositions comprising the following: a) an isolated polypeptide comprising a positive-stranded RNA virus core-like antigen protein joined to an amino-terminal portion of an adjacent nucleic acid region of the positive-stranded RNA virus, wherein the amino-terminal portion of the adjacent nucleic acid region is sized such that the polypeptide has an epitopic configuration specific to an unprocessed core-like-adjacent nucleic acid region of the positive-stranded RNA virus (this polypeptide is sometimes referred to herein as a "core-like antigen-adjacent protein"); and b) an isolated nonstructural protein of the positive-stranded RNA virus.

In preferred embodiments that relate to each of the aspects of the present invention, the positive-stranded RNA virus is selected from the group consisting of Togaviridae, Coronaviridae, Retroviridae, Picornaviridae, Caliciviridae and Flaviviridae, further preferably from the group consisting of Hepatitis C virus, the Human Immunodeficiency virus (HIV) and the Human T-cell Leukemia virus (HTLV). Alternatively, the positive-stranded RNA virus is any positive-stranded RNA virus other than HCV. In other preferred embodiments, the composition is produced by a suitable prokaryotic host cell, typically a bacterium, and preferably an E. coli BL21 (DE3). Alternatively, the isolated polypeptide is produced by a suitable eukaryotic host cell that is unable to process the isolated polypeptide.

In another aspect, the present invention provides a method of making a composition comprising an isolated, substantially complete, unprocessed polyprotein from a positive-stranded RNA virus. This aspect also provides a method of making multiple polypeptides obtained from a positive-stranded RNA virus, comprising the following steps: a) introducing into a first suitable host cell a first expression vector capable of expressing a nucleic acid molecule encoding an isolated polypeptide comprising a positive-stranded RNA virus core-like antigen protein joined to an amino-terminal portion of an adjacent nucleic acid region of the positive-stranded RNA virus, wherein the amino-terminal portion of the adjacent nucleic acid region is sized such that the polypeptide has an epitopic configuration specific to an unprocessed core-like-adjacent nucleic acid region of the positive-stranded RNA virus, b)incubating the first host cell under conditions suitable for the expression vector to produce the polypeptide, c) purifying the polypeptide to provide a purified polypeptide, and d) introducing into a second suitable host cell a second expression vector capable of expressing a nucleic acid molecule encoding an isolated nonstructural protein of the positive-stranded RNA virus, e) incubating the second host cell under conditions suitable for the nucleic acid molecule to produce the nonstructural protein, f) purifying the nonstructural protein to provide an purified nonstructural protein, and then g) combining the purified polypeptide and the purified nonstructural protein in the composition.

In a preferred embodiment, the method further comprises a) introducing into a suitable host cell an expression vector capable of expressing a first nucleic acid molecule encoding an isolated polypeptide comprising a positive-stranded RNA virus core-like antigen protein joined to an amino-terminal portion of an adjacent nucleic acid region of the positive-stranded RNA virus, wherein the amino-terminal portion of the adjacent nucleic acid region is sized such that the polypeptide has an epitopic configuration specific to an unprocessed core-like-adjacent nucleic acid region of the positive-stranded RNA virus, b) incubating the host cell under conditions suitable for the expression vector to produce the polypeptide and the nonstructural protein, and c) purifying the polypeptide and the nonstructural protein to provide a purified polypeptide and a purified nonstructural protein. In another preferred embodiment, the method further comprises binding the inventive polypeptide(s) to a solid substrate.

In a further aspect, the present invention provides a composition comprising the isolated, substantially complete, unprocessed polyprotein from a positive-stranded RNA virus wherein the polyprotein is bound to a solid substrate. Alternatively, the composition comprises the core-like antigen-adjacent protein bound to a solid substrate, preferably further comprising a nonstructural protein of the positive-stranded RNA virus bound to the solid substrate.

In another preferred embodiment, an assay for the detection of a positive-stranded RNA virus in a sample, comprising: a) providing an isolated polypeptide comprising a positive-stranded RNA virus core-like antigen-adjacent protein, b) contacting the isolated polypeptide with the sample under conditions suitable and for a time sufficient for the polypeptide to bind to one or more antibodies specific for the positive-stranded RNA virus present in the sample, to provide an antibody-bound polypeptide, and c) detecting the antibody-bound polypeptide, and therefrom determining that the sample contains positive-stranded RNA virus. In an alternative embodiment, the method comprises, a) providing an isolated polypeptide comprising an isolated, substantially complete, unprocessed polyprotein from a positive-stranded RNA virus, b) contacting the isolated polypeptide with the sample under conditions suitable and for a time sufficient for the polypeptide to bind to one or more antibodies specific for the positive-stranded RNA virus present in the sample, to provide an antibody-bound polypeptide, and c) detecting the antibody-bound polypeptide, and therefrom determining that the sample contains positive-stranded RNA virus.

In a preferred embodiment, the method further comprises a) in step a), providing a nonstructural protein of the positive-stranded RNA virus bound to the solid substrate, b) in step b), contacting the nonstructural protein with the sample under conditions suitable and for a time sufficient for the nonstructural protein to bind to one or more antibodies specific for the positive-stranded RNA virus present in the sample, to provide an antibody-bound positive-stranded RNA virus nonstructural protein, and c) in step c), detecting one or both of the antibody-bound polypeptide or the antibody-bound nonstructural protein, and therefrom determining that the sample contains positive-stranded RNA virus.

In another preferred embodiment, the assay further comprises the step of binding the isolated polypeptide, the nonstructural protein, or the polyprotein to a solid substrate. In another preferred embodiment, the sample is an unpurified sample, typically from an animal, and preferably from a human being. In yet other preferred embodiments, the assay is selected from the group consisting of a countercurrent immuno-electrophoresis (CIEP) assay, a radioimmunoassay, a radioimmunoprecipitation, an enzyme-linked immuno-sorbent assay (ELISA), a dot blot assay, an inhibition or competition assay, a sandwich assay, an immunostick (dip-stick) assays, a simultaneous assay, an immunochromatographic assay, an immunofiltration assay, a latex bead agglutination assay, an immunofluorescent assay, a biosensor assay, and a low-light detection assay. Still further, the assay is preferably not a western blot assay.

In still a further aspect, the present invention provides a method of producing an antibody, comprising the following steps: a) administering to an animal an isolated polypeptide comprising a positive-stranded RNA virus core-like antigen protein joined to an amino-terminal portion of an adjacent nucleic acid region of the positive-stranded RNA virus, wherein the amino-terminal portion of the adjacent nucleic acid region is sized such that the polypeptide has an epitopic configuration specific to an unprocessed core-like-adjacent nucleic acid region of the positive-stranded RNA virus, and b) isolating the antibodies to the polypeptide. Alternatively, the invention provides a method of producing an antibody, comprising the following steps: a) administering to an animal an isolated polypeptide comprising an isolated, substantially complete, unprocessed polyprotein from a positive-stranded RNA virus, and b) isolating the antibodies to the polyprotein.

The present invention also provides the antibody produced according to either of the above methods, as well as an antibody to the other proteins disclosed herein (such as the nonstructural proteins). Preferably, the antibodies are bound to a solid substrate.

In yet another aspect, the present invention provides an assay for the detection of a positive-stranded RNA virus in a sample, comprising: a) contacting the sample with one or more of the antibodies described above under conditions suitable and for a time sufficient for the given antibody to bind its antigen protein, to provide a bound antibody, and b) detecting the bound antibody, and therefrom determining that the sample contains positive-stranded RNA virus.

In a preferred embodiment, the sample is an unpurified sample, typically from an animal, and preferably from a human being. In yet other preferred embodiments, the assay is selected from the group consisting of a countercurrent immuno-electrophoresis (CIEP) assay, a radioimmunoassay, a radioimmunoprecipitation, an enzyme-linked immuno-sorbent assay (ELISA), a dot blot assay, an inhibition or competition assay, a sandwich assay, an immunostick (dip-stick) assays, a simultaneous assay, an immunochromatographic assay, an immunofiltration assay, a latex bead agglutination assay, an immunofluorescent assay, a biosensor assay, and a low-light detection assay. Still further, the assay is preferably not a western blot assay.

In yet a further aspect, the present invention provides a composition capable of eliciting an immune response in an animal comprising an isolated polypeptide comprising a positive-stranded RNA virus core-like antigen-adjacent protein, in combination with a pharmaceutically acceptable carrier or diluent. Preferably, the composition further comprises a nonstructural protein from the positive-stranded RNA virus. In an alternative aspect, the composition capable of eliciting an immune response in an animal comprises an isolated, substantially complete, unprocessed polyprotein from a positive-stranded RNA virus, in combination with a pharmaceutically acceptable carrier or diluent.

Preferably, for each of the immune-active aspects (as well as the other aspects) of the invention, the animal is a human being.

In still yet a further aspect, the present invention provides a vaccine against a positive-stranded RNA virus comprising an isolated polypeptide comprising a positive-stranded RNA virus core-like antigen-adjacent protein, in combination with a pharmaceutically acceptable carrier or diluent. Preferably, the composition fuirther comprises a nonstructural protein from the positive-stranded RNA virus. In an alternative aspect, the vaccine against a positive-stranded RNA virus comprises an isolated, substantially complete, unprocessed polyprotein from a positive-stranded RNA virus, in combination with a pharmaceutically acceptable carrier or diluent.

The present invention also provides a method of inducing an immune response in an animal comprising administering to the animal an isolated polypeptide comprising a positive-stranded RNA virus core-like antigen-adjacent protein, in combination with a pharmaceutically acceptable carrier or diluent. Preferably, the method further comprises administering a nonstructural protein from the positive-stranded RNA virus. In an alternative aspect, the method of inducing an immune response in an animal comprises administering to the animal an isolated, substantially complete, unprocessed polyprotein from a positive-stranded RNA virus, in combination with a pharmaceutically acceptable carrier or diluent.

The present invention further provides a method of vaccinating an animal comprising administering to the animal an isolated polypeptide comprising a positive-stranded RNA virus core-like antigen-adjacent protein, in combination with a pharmaceutically acceptable carrier or diluent. Preferably, the method fuirther comprises administering a nonstructural protein from the positive-stranded RNA virus. In an alternative aspect, the method of vaccinating an animal comprises administering to the animal an isolated, substantially complete, unprocessed polyprotein from a positive-stranded RNA virus, in combination with a pharmaceutically acceptable carrier or diluent.

In yet another aspect, the present invention provides a kit for the detection of a positive-stranded RNA virus, the kit comprising a) an isolated polypeptide comprising a positive-stranded RNA virus core-like antigen protein joined to an amino-terminal portion of an adjacent nucleic acid region of the positive-stranded RNA virus, wherein the amino-terminal portion of the adjacent nucleic acid region is sized such that the polypeptide has an epitopic configuration specific to an unprocessed core-like-adjacent nucleic acid region of the positive-stranded RNA virus, bound to a solid substrate, and b) means for detecting the isolated polypeptide. Preferably, the kit comprises a nonstructural protein from the positive-stranded RNA virus and means for detecting the nonstructural protein. Alternatively, the kit for the detection of a positive-stranded RNA virus comprises a) an isolated, substantially complete, unprocessed polyprotein from a positive-stranded RNA virus, bound to a solid substrate, and b) means for detecting the isolated polyprotein.

In an alternative aspect, the present invention provides a kit for the detection of a positive-stranded RNA virus comprising: a) one or more of the antibodies discussed above, and b) means for detecting the antibody(s).

The kits may also comprise a)the composition capable of eliciting an immune response, or the vaccine, and b) means for administering the composition or vaccine to the animal.

Turning to another aspect, the present invention provides a positive-stranded RNA virus-derived composition comprising the following: a) an isolated polypeptide comprising a positive-stranded RNA virus core-like antigen protein joined to an adjacent nucleic acid region of the positive-stranded RNA virus, wherein the adjacent nucleic acid region is sized such that the polypeptide has an epitopic configuration specific to an unprocessed core-like-adjacent nucleic acid region of the positive-stranded RNA virus; and b) a second protein capable of cooperatively interacting with the positive-stranded RNA virus core-like antigen protein joined to the adjacent nucleic acid region of the positive-stranded RNA virus to increase the antigenicity of the positive-stranded RNA virus core-like antigen protein joined to the adjacent nucleic acid region of the positive-stranded RNA virus. The present invention also provides a method of making such composition comprising multiple polypeptides, including one or both of the polypeptide described above; the proteins may be derived from the same or different positive-stranded RNA viruses.

The present invention also provides a composition comprising a first isolated protein from the positive-stranded RNA virus and a second isolated protein from the positive-stranded RNA virus (preferably from the same positive-stranded RNA virus), wherein the first and second proteins are selected, in accordance with methods set forth below for other embodiments of the claimed invention, such that the first and second proteins provide a synergistic effect for the detection of the positive-stranded RNA virus and/or immunoenhancement of an animal against the positive-stranded RNA virus.

The invention also provides the isolated polypeptide comprising a positive-stranded RNA virus core-like antigen protein joined to an adjacent nucleic acid region of the positive-stranded RNA virus, wherein the adjacent nucleic acid region is sized such that the polypeptide has an epitopic configuration specific to an unprocessed core-like-adjacent nucleic acid region of the positive-stranded RNA virus, bound to a solid substrate, either alone or in combination with a second protein capable of cooperatively interacting with the positive-stranded RNA virus core-like antigen protein joined to the adjacent nucleic acid region of the positive-stranded RNA virus to increase the antigenicity of the positive-stranded RNA virus core-like antigen protein joined to the adjacent nucleic acid region of the positive-stranded RNA virus of the positive-stranded RNA virus bound to the solid substrate.

In yet another aspect, the present invention provides an assay for the detection of a positive-stranded RNA virus in a sample, comprising: a) providing an isolated polypeptide comprising a positive-stranded RNA virus core-like antigen protein joined to adjacent nucleic acid region of the positive-stranded RNA virus, wherein the adjacent nucleic acid region is sized such that the polypeptide has an epitopic configuration specific to an unprocessed core-like-adjacent nucleic acid region of the positive-stranded RNA virus, b) contacting the isolated polypeptide with the sample under conditions suitable and for a time sufficient for the polypeptide to bind to one or more antibodies specific for the positive-stranded RNA virus present in the sample, to provide an antibody-bound polypeptide, and c) detecting the antibody-bound polypeptide, and therefrom determining that the sample contains positive-stranded RNA virus. The assay may also comprise, a) in step a), providing a a second protein capable of cooperatively interacting with the positive-stranded RNA virus core-like antigen protein joined to the adjacent nucleic acid region of the positive-stranded RNA virus to increase the antigenicity of the positive-stranded RNA virus core-like antigen protein joined to the adjacent nucleic acid region of the positive-stranded RNA virus, bound to the solid substrate, b) in step b), contacting the second protein with the sample under conditions suitable and for a time sufficient for the second protein to cooperatively interact with the positive-stranded RNA virus core-like antigen protein joined to the adjacent nucleic acid region of the positive-stranded RNA virus, and c) in step c), detecting bound antibodies, and therefrom determining that the sample contains positive-stranded RNA virus.

In a preferred embodiment, the assay further comprises the step of binding the isolated polypeptide or the second protein to a solid substrate. Further preferably, the assay is selected from the group consisting of a countercurrent immuno-electrophoresis (CIEP) assay, a radioimmunoassay, a radioimmunoprecipitation, an enzyme-linked immunosorbent assay (ELISA), a dot blot assay, an inhibition or competition assay, a sandwich assay, an immunostick (dipstick) assays, a simultaneous assay, an immunochromatographic assay, an immunofiltration assay, a latex bead agglutination assay, an immunofluorescent assay, a biosensor assay, and a low-light detection assay, but is not a western blot assay.

The present invention also provides a method of producing an antibody, comprising a) administering to an animal an isolated polypeptide comprising a positive-stranded RNA virus core-like antigen protein joined to an adjacent nucleic acid region of the positive-stranded RNA virus, wherein the adjacent nucleic acid region is sized such that the polypeptide has an epitopic configuration specific to an unprocessed core-like-adjacent nucleic acid region of the positive-stranded RNA virus, and b) isolating the antibodies to the polypeptide. The method may further comprise administering to the animal a second protein capable of cooperatively interacting with the positive-stranded RNA virus core-like antigen protein joined to the adjacent nucleic acid region of the positive-stranded RNA virus to increase the antigenicity of the positive-stranded RNA virus core-like antigen protein joined to the adjacent nucleic acid region of the positive-stranded RNA virus. The present invention features an antibody produced as above, which antibodies may be bound to a solid substrate. The antibodies may also be used in assays, also as described above.

In yet another aspect, the present invention provides a composition capable of eliciting an immune response in an animal comprising an isolated polypeptide comprising a positive-stranded RNA virus core-like antigen protein joined to an adjacent nucleic acid region of the positive-stranded RNA virus, wherein the adjacent nucleic acid region is sized such that the polypeptide has an epitopic configuration specific to an unprocessed core-like-adjacent nucleic acid region of the positive-stranded RNA virus, in combination with a pharmaceutically acceptable carrier or diluent. The composition may further comprise a second protein capable of cooperatively interacting with the positive-stranded RNA virus core-like antigen protein joined to the adjacent nucleic acid region of the positive-stranded RNA virus to increase the antigenicity of the positive-stranded RNA virus core-like antigen protein joined to the adjacent nucleic acid region of the positive-stranded RNA virus. Preferably, the composition is a vaccine.

The present invention also provides a method of inducing an immune response in an animal comprising administering to the animal an isolated polypeptide comprising a positive-stranded RNA virus core-like antigen protein joined to an adjacent nucleic acid region of the positive-stranded RNA virus, wherein the adjacent nucleic acid region is sized such that the polypeptide has an epitopic configuration specific to an unprocessed core-like-adjacent nucleic acid region of the positive-stranded RNA virus, in combination with a pharmaceutically acceptable carrier or diluent. Preferably, the method further comprises administering a second protein capable of cooperatively interacting with the positive-stranded RNA virus core-like antigen protein joined to the adjacent nucleic acid region of the positive-stranded RNA virus to increase the antigenicity of the positive-stranded RNA virus core-like antigen protein joined to the adjacent nucleic acid region of the positive-stranded RNA virus. Further preferably, the method comprises a vaccination.

In another aspect, the present invention provides a kit for the detection of a positive-stranded RNA virus comprising: a) an isolated polypeptide comprising a positive-stranded RNA virus core-like antigen protein joined to an adjacent nucleic acid region of the positive-stranded RNA virus, wherein the adjacent nucleic acid region is sized such that the polypeptide has an epitopic configuration specific to an unprocessed core-like-adjacent nucleic acid region of the positive-stranded RNA virus, bound to a solid substrate, and b) means for detecting the isolated polypeptide. Preferably, the kit further comprises a second protein capable of cooperatively interacting with the positive-stranded RNA virus core-like antigen protein joined to the adjacent nucleic acid region of the positive-stranded RNA virus to increase the antigenicity of the positive-stranded RNA virus core-like antigen protein joined to the adjacent nucleic acid region of the positive-stranded RNA virus and means for detecting the second protein.

Alternatively, the kit for the detection of a positive-stranded RNA virus may comprise: a) an antibody produced as described above, and b) means for detecting the antibody.

These and other aspects of the present invention will become evident upon reference to the following detailed description and attached drawings. In addition, as noted above, various references are set forth throughout the present specification that describe in more detail certain procedures or compositions (e.g., plasmids, etc.); such references are incorporated by reference in their entirety.

BRIEF DESCRIPTION OF THE DRAWINGS

FIG. 1A depicts the nucleotide sequence of a nucleic acid molecule encoding a polypeptide comprising an HCV core antigen protein joined to an amino-terminal portion of an HCV envelope region (SEQ ID NO: 7).

FIG. 1B depicts the amino acid sequence encoded by the nucleotide sequence depicted in FIG. 1A (SEQ ID NO: 8).

FIG. 3A depicts the nucleotide sequence of a nucleic acid molecule encoding a polypeptide comprising an NS5 nonstructural region (SEQ ID NO: 9).

FIG. 3B depicts the amino acid sequence encoded by the nucleotide sequence depicted in FIG. 3A (SEQ ID NO: 10).

FIG. 4 shows the structure of the expression vector pEN-1, which was constructed by inserting a cDNA encoding an NS5 nonstructural region into a plasmid. The figure also shows a restriction map illustrating certain significant features of the vector pEN-1.

DETAILED DESCRIPTION OF THE INVENTION

Figure 2:
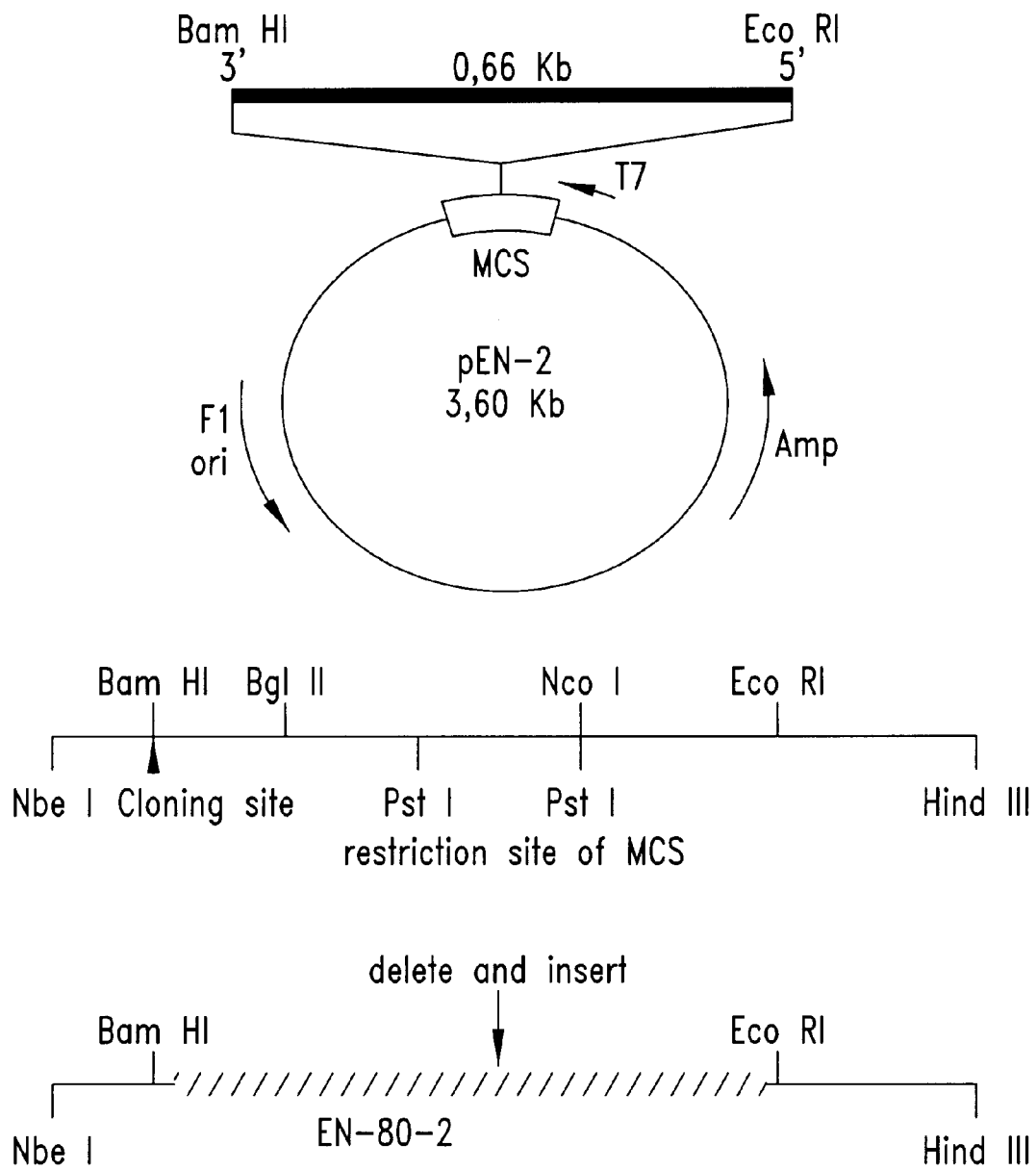
FIG. 2 shows the structure of the expression vector pEN-2, which was constructed by inserting a cDNA encoding an HCV core antigen protein joined to an amino-terminal portion of an HCV envelope region into a plasmid. The figure also shows a restriction map illustrating certain significant features of the vector pEN-2.

The present invention is based on the discovery that the unprocessed polyprotein initially translated from the genome of a positive-stranded RNA virus contains epitopic configurations that are not retained in the processed proteins. In particular, the core protein region (or other protein encoded by the viral genome that serves the equivalent purpose as the "core" protein) loses an epitopic configuration upon processing at the cleavage site between the genomic region (e.g., gene) encoding the core protein and the genomic region encoding the protein adjacent the amino-terminal end of the core protein, such as the envelope protein in HCV. As discussed below in the Examples portion of the present disclosure, the unprocessed epitopic configuration of the core region provides a surprisingly improved ability to detect the presence of the positive-stranded RNA virus, or antibodies to the positive-stranded RNA virus, in a sample, including an unpurified sample or a sample of very small volume (which can be particularly helpful when testing a sample from an infant or other person having very little blood (or other suitable material) available for testing).

Even more surprising, combining the unprocessed core region with a non-structural protein (such as an NS5 protein or an unprocessed NS3-NS4 fusion protein from HCV) results in a synergistic effect that greatly enhances the already improved sensitivity and specificity provided by the unprocessed core region.

These significant advantages in antigenicity and epitopic configuration also provide significantly enhanced compositions and methods for the induction of immune responses in an animal, and are expected to provide significantly enhanced vaccination of such an animal.

Accordingly, the present invention features compositions and methods utilizing an isolated, substantially complete, unprocessed polyprotein from a positive-stranded RNA virus.

The present invention also features compositions and methods utilizing an isolated polypeptide comprising the positive-stranded RNA virus core antigen protein joined to an amino-terminal portion of the adjacent protein of the positive-stranded RNA virus, wherein the amino-terminal portion of the positive-stranded RNA virus envelope region is sized such that the polypeptide has an epitopic configuration specific to an unprocessed core-adjacent protein region of the positive-stranded RNA virus. The present invention additionally features the combination of such an unprocessed core-adjacent protein region in a composition or method with a nonstructural protein, thereby providing surprisingly sensitive and specific interactions with the given positive-stranded RNA virus.

The present invention provides the first discovery that the full polyprotein does have unique configurations, and that such configurations result in antigenically important differences. The present invention also provides the first discovery that a lost epitopic configuration occurs in the core protein-adjacent protein region.

An "isolated, substantially complete, unprocessed polyprotein" from a positive-stranded RNA virus is the polyprotein that is initially translated from the genome of the positive-stranded RNA virus. Such polyprotein has not been subjected to processing, and thus the processing sites between the proteins of the polyprotein are not cleaved. The polyprotein is also isolated, which means that the polyprotein has been separated from its encoding genome. The polyprotein is substantially complete when it retains all of the functional elements necessary to provide the immune-active features of the present invention, particularly epitopic configuration(s) that are present only in the polyprotein and not in the processed proteins or subunits that are obtained from the polyprotein. However, with respect to this and other proteins of the present invention, it is within the skill of the art to make conservative amino acid substitutions, or insignificant amino acid additions, modifications or deletions, that may change the amino acid sequence of the protein but do not significantly alter the functioning of the protein (i.e., the unprocessed epitopic configuration is retained). However, such modifications may, when desired, delete the processing signals and/or sites of the protein. These modifications are discussed further below. The completeness of the polyprotein may be determined, for example, by SDS-PAGE followed by amino acid sequencing. The completeness may also be determined by utilizing the polyprotein in question in one or more of the assays discussed below, and detecting effects of epitopic configurations specific to the unprocessed state.

A "core-like" protein is a structural protein that provides the same type of functions as the core protein of HCV. Examples of "core-like" proteins from other viruses include the Japanese encephalitis virus core protein and the HIV gag protein. A "core-like antigen protein" is a structural "core-like" protein that includes the portion of the core-like protein that displays the antigenicity of the core-like protein. Although alteration of epitopic configuration upon processing was not known in the art, core-like proteins generally, and regions of the core-like proteins that can be important to antigenicity, are well known in the art (see, e.g., Okamoto et al. *J. Virol.* 188:331, 1992; Wang, U.S. Pat. No. 5,106,726). A core-like antigen protein may be determined for a desired positive-stranded RNA virus, for example, by ELISA or western blotting, or both, for traditional core-type antigenic reactivity, as is well known in the art. The core-like antigen protein may also be determined by SDS-PAGE followed by amino acid sequencing.

Typically, the core-like antigen protein is joined to an amino-terminal portion of the adjacent protein or peptide region of the positive-stranded RNA virus to provide the unprocessed "core-like antigen-adjacent protein" of the invention. However, in some embodiments, particularly where the core-like protein is not the first protein region of the polyprotein, the core-like protein is joined to a carboxyl-terminal portion of the adjacent protein of the positive-stranded RNA virus in unprocessed form to provide the inventive unprocessed core-like antigen-adjacent protein of the invention. In unprocessed form means that the core-like region and the adjacent region are typically, and preferably, maintained precisely as they are joined (i.e., encoded) in a native positive-stranded RNA virus. As with the polyprotein and other proteins herein, the core-like antigen protein may be insignificantly modified without changing the inventive functioning of the core-like antigen protein.

The portion of the "adjacent protein" that is adjacent the core-like antigen protein is sized such that the fusion protein has an epitopic configuration specific to an unprocessed core-like-adjacent protein of the positive-stranded RNA virus. Thus, typically, the amino-terminal portion of the adjacent protein region must be of sufficient length to permit the fusion protein to display the transient epitopic configuration specific to the unprocessed core-like region.

To determine whether a given polypeptide displays the epitopic configuration of the inventive core-like antigen-adjacent protein, a core-like antigen-adjacent protein in question can be included in a panel of core-like antigen-adjacent proteins comprising an established core-like antigen-adjacent protein, such as EN-80-2. The panel is placed in a series of wells on a microtiter plate. The panel can also include other core-like antigen-adjacent proteins having different lengths of adjacent protein. In a separate well is placed an established nonstructural, or other, protein capable of synergistic cooperation with the core-like antigen-adjacent protein, such as EN-80-1. An antiserum is selected for the established core-like antigen-adjacent protein that reacts weakly with the established core-like antigen-adjacent protein and that also is nonreactive with the established nonstructural protein. The basis for selection is that the antiserum will react with the separated proteins as expected, but the antiserum will react much more strongly when both a suitable core-like antigen-adjacent protein and the established nonstructural protein are present in the sample. Many examples, such as G614 (diluted 8-fold), G614 (diluted 16-fold), G615 (diluted 8-fold), G615 (diluted 16-fold), and 8-5, of such an antiserum are set forth below in the Examples. The antiserum is introduced to the sample proteins under conditions suitable for elicitation and detection of a reaction between the antiserum and the given protein, and detect and measure such response. The established nonstructural protein is then combined with each member of the core-like antigen-adjacent protein panel. Next, the antiserum is introduced to the combined proteins under conditions suitable for elicitation and detection of a reaction between the antiserum and the proteins, and such response is detected and measured. Those core-like antigen-adjacent proteins that provide a cooperative effect are suitable for use in the present invention. Preferably, the antiserum will react at least about 1.25 or 1.5 times as strongly with the combined proteins when compared to the additive reaction of the antiserum with each protein, alone. Further preferably, the antiserum will react at least about twice as strongly. Each of the above-recited steps is routine in the art, in light of the present specification.

The core-like antigen-adjacent protein is preferably isolated, which means that the core-like antigen-adjacent protein is separated from the remainder of the polyprotein originally translated from the genome of the positive-stranded RNA virus. The core-like antigen-adjacent protein is also preferably separated from its encoding nucleic acid molecule.

In a preferred embodiment, the core-like antigen-adjacent protein of the present invention is used in combination with a second protein. The second protein is preferably from a positive-stranded RNA virus, is further preferably from the same positive-stranded RNA virus as the core-like antigen-adjacent protein, and is most preferably a nonstructural protein from a positive-stranded RNA virus (preferably from the same positive-stranded RNA virus as the core-like antigen-adjacent protein).

In one preferred embodiment, the second protein is a nonstructural protein. In positive stranded RNA viruses other than HCV, the nonstructural proteins may be referred to by other names, as is well known in the art. For the purposes of the present specification, all such nonstructural-like proteins shall be referred to herein as "Inonstructural proteins." As noted above, the nonstructural coding regions of positive-stranded RNA viruses are well known in the art.

The determination of an appropriate second protein that is suitable for use with the core-like antigen-adjacent protein, which second protein may include portions of nonstructural coding regions comprising more than one nonstructural protein (or less than all of one nonstructural protein), can be performed as follows.

A second protein in question can be included in a panel of second proteins comprising an established second protein, such as EN-80-2 EN-80-1. The panel is placed in a series of wells on a microtiter plate. The panel can also include other second proteins having different lengths of adjacent protein. In a separate well is placed an established core-like antigen-adjacent protein capable of synergistic cooperation with the second protein, such as EN-80-1 EN-80-2. An antiserum is selected for the established second protein that reacts weakly with the established second protein and that also is nonreactive with the established core-like antigen-adjacent protein. The basis for selection is that the antiserum will react with the separated proteins as expected, but the antiserum will react much more strongly when both a suitable second protein and the established core-like antigen-adjacent protein are present in the sample. Many examples of such an antiserum are set forth below in the Examples. The antiserum is introduced to the sample proteins under conditions suitable for elicitation and detection of a reaction between the antiserum and the given protein, and such response is detected and measured. The established core-like antigen-adjacent protein is combined with each member of the second protein panel. Next, the antiserum is introduced to the combined proteins under conditions suitable for elicitation and detection of a reaction between the antiserum and the proteins, and such response is detected and measured. Those second proteins that provide a cooperative effect are suitable for use in the present invention. Each of the above-recited steps is routine in the art, in light of the present specification.

The present invention also provides antibodies, preferably monoclonal antibodies, to the substantially complete polyprotein, the core-like antigen-adjacent protein, and/or nonstructural protein of the present invention, as well as other proteins of the present invention. The antibodies are preferably used in combination to provide particularly sensitive and specific detection of the positive-stranded RNA virus in a sample.

Still further, the present invention provides compositions and methods for the elicitation on an immune response in an animal (either humoral, cellular, or both). Even further, the compositions and methods can vaccinate an animal against the positive-stranded RNA virus.

Preferably, the methods and compositions of the present invention, including those for detection, immune response elicitation and vaccination, are applied to a human being.

One example of the present invention is the Hepatitis C virus (HCV). The following discussion focuses generally on HCV, and even further on the HCV core antigen protein joined to an amino-terminal portion of an HCV envelope region. The discussion also focuses on such core antigen-envelope region in combination with an HCV nonstructural protein (particularly the HCV NS5 and NS3-NS4 nonstructural proteins), or in combination with a second protein from another positive-stranded RNA virus (particularly the HIV envelope protein and the HTLV-I envelope protein). As noted above, this discussion is predictive of the results to be obtained with the core-like antigen-adjacent proteins of positive-stranded RNA viruses generally. The discussion is also predictive of the results to be obtained with the substantially complete polyprotein of positive-stranded RNA viruses generally, and the substantially complete polyprotein of HCV in particular.

Nucleic Acid Molecules Encoding the Unprocessed Polypeptides, and Other Polypeptides, of the Invention As noted above, the present invention includes a nucleic acid molecule encoding a polypeptide comprising a substantially complete positive-stranded RNA virus polyprotein. The present invention also provides a nucleic acid molecule encoding a polypeptide comprising a core-like antigen-adjacent protein, such as the HCV core antigen protein joined to an amino-terminal portion of the HCV envelope region. The present invention further provides a nucleic acid molecule encoding a polypeptide comprising a nonstructural protein of such positive-stranded RNA virus. In a preferred embodiment, the nucleic acid molecule is DNA.

In a preferred embodiment, the nucleic acid molecule is a DNA molecule encoding an unprocessed core antigen-envelope protein that was isolated from nucleic acid sequences present in the plasma of an HCV infected patient. As discussed further below, the isolation of the molecule included the steps of isolating viral particles from the patient's plasma, extracting and purifying the viral nucleic acid sequences, and then cloning the desired DNA molecule via a Polymerase Chain Reaction (PCR) technique. The primers used for cloning were as follows:

(i) 5'-GGATCCATGAGCACAAATCCTAAA CCT-3' (SEQ ID NO. 1)

and (ii) 5'-GAATTCGGTGTGCATGATCATGTC CGC-3' (SEQ ID NO. 2)

The cloned DNA molecule was sequenced in order to confirm its identity. The molecule thus obtained was designated EN-80-2. The DNA sequence of the molecule EN-80-2 is given in FIG. 1A (SEQ ID NO. 7), and has 669 bp. The amino acid sequence of the molecule EN-80-2 is given in FIG. 1B (SEQ ID NO. 8), and has 223 residues. The molecule EN-80-2, in *E. coli* strain BL21 (DE3), was deposited with the American Type Culture Collection (ATCC) Rockville, Md. 20852, on Jul. 14, 1993, and has been accorded ATCC Designation 55451. The culture has been deposited under conditions that assure that access to the cell line will be available during the pendency of the present patent application to one determined by the Commissioner of Patents and Trademarks to be entitled thereto under 37 C.F.R. § 1.14 and 35 U.S.C. § 122 for a period of 30 years, or 5 years after the last request, or for the effective life of the patent, whichever is longer. All restrictions on the availability to the public of the deposited culture will be irrevocably removed upon the issuance of a patent from the above-identified patent application. The deposit will be replaced if it ever becomes nonviable.

In another preferred embodiment, the nucleic acid molecule is a DNA molecule encoding an HCV NS5 nonstructural protein that was isolated from nucleic acid sequences present in the plasma of an HCV infected patient. As with the isolation of the unprocessed core antigen-envelope protein discussed above (although with a different patient), the isolation included the steps of isolating viral particles from the patient's plasma, extracting and purifying the viral nucleic acid sequences, and then cloning the desired DNA molecule via a Polymerase Chain Reaction (PCR) technique. The primers used in the PCR were as follows:

(i) 5'-GGATCCCGGTGGAGGATGAGAGGG
    AAATATCCG-3'                          (SEQ ID NO. 3)

and (ii) 5'-GAATTCCCGGACGTCCTTCGCCCCGTAGCCAAATTT-
    3'                                   (SEQ ID NO. 4)

The isolated DNA molecule was subjected to sequence analysis in order to confirm its identity. The molecule thus obtained was designated EN-80-1. The DNA sequence of the molecule EN-80-1 is given in FIG. 3A (SEQ ID NO. 9) and has 803 bp. The amino acid sequence of the molecule EN-80-1 is given in FIG. 3B (SEQ ID NO. 10), and has 267 residues. The molecule EN-80-1, in *E. coli* strain BL21 (DE3), was deposited with the American Type Culture Collection (ATCC) Rockville, Md. 20852, on Jul. 14, 1993, and has been accorded ATCC Designation 55450. The culture has been deposited under conditions that assure that access to the cell line will be available during the pendency of the present patent application to one determined by the Commissioner of Patents and Trademarks to be entitled thereto under 37 C.F.R. § 1.14 and 35 U.S.C. § 122 for a period of 30 years, or 5 years after the last request, or for the effective life of the patent, whichever is longer. All restrictions on the availability to the public of the deposited culture will be irrevocably removed upon the issuance of a patent from the above-identified patent application. The deposit will be replaced if it ever becomes nonviable.

FIG. 2 depicts an expression plasmid, pEN-2, that contains the DNA molecule encoding the unprocessed core antigen-envelope protein isolated using the primers SEQ ID Nos. 1 and 2, discussed above. FIG. 4 depicts an expression plasmid, pEN-1, that contains the DNA molecule encoding the NS5 nonstructural protein isolated using the primers SEQ ID Nos. 1 and 2, discussed above.

This general procedure has also been used to isolate a representative nucleic acid molecule from the NS3-NS4 nonstructural region of HCV. See also Simmonds, *Lancet* 336: 1469–1472, 1990. The primers used for the cloning were as follows:

(i("ED3")) 5'-CACCCAGACAGTCGATTTC
    AG-3'                               (SEQ ID NO. 5)

and (ii("ED4")) 5'-GTATTTGGTGACTGGGTGC
    GTC-3'                              (SEQ ID NO. 6)

The molecule thus obtained was designated EN-80-4. The polypeptide encoded by the isolated molecule has a molecular weight of about 20,000 Daltons as measure by electrophoresis through SDS-PAGE.

Additional examples of polypeptides useful as the second protein include the HIV envelope protein (molecular wieght about 18,000 daltons) and the HTLV envelope protein (molecular wieght about 18,000 daltons).

The present invention provides for the manipulation and expression of the above described nucleic acid molecules by culturing host cells containing a construct capable of expressing the above-described genes.

Numerous vector constructs suitable for use with the nucleic acid molecules of the present invention can be prepared as a matter of convenience. Within the context of the present invention, a vector construct is understood to typically refer to a DNA molecule, or a clone of such a molecule (either single-stranded or double-stranded), that has been modified through human intervention to contain segments of DNA combined and juxtaposed in a manner that as a whole would not otherwise exist in nature. Vector constructs of the present invention comprise a first DNA segment encoding one or more of an unprocessed core-like antigen-adjacent protein and a nonstructural protein of a positive stranded RNA virus operably linked to additional DNA segments required for the expression of the first DNA segment. Within the context of the present invention, additional DNA segments will include a promoter and will generally include transcription terminators, and may further include enhancers and other elements. See WO 94/25597 and WO/25598.

Mutations in nucleotide sequences constructed for expression of the inventive proteins preferably preserve the reading frame of the encoding sequences. Furthermore, the mutations will preferably not create complementary regions that could hybridize to produce secondary mRNA structures, such as loops or hairpins, that would adversely affect translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed mutants screened for indicative biological activity.

Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution or deletion.

Alternatively, oligonucleotide-directed, site-specific mutagenesis procedures may be employed to provide an altered gene having particular codons altered according to the substitution, deletion, or insertion required. Exemplary methods of making the alterations set forth above are disclosed by Walder et al. (*Gene* 42:133, 1986); Bauer et al. (*Gene* 37:73, 1985); Craik (*BioTechniqies*, January 1985, 12–19); Smith et al. (*Genetic Engineering: Principles and Methods*, Plenum Press, 1981); and Sambrook et al. (supra).

The primary amino acid structure of the above described proteins may also be modified by forming covalent or aggregative conjugates with other chemical moieties, such as glycosyl groups, lipids, phosphate, acetyl groups, or with other proteins or polypeptides, provided that such modifications should not interfere with the antigenicity of the proteins. (See U.S. Pat. No. 4,851,341; see also Hopp et al., *Bio/Technology* 6:1204, 1988). For example, such modifications should not interfere with the epitopic configuration (including access to the epitope and other antigenic considerations) specific to the unprocessed core-like antigen-adjacent protein.

A preferred type of vector construct is known as an expression vector. As noted above, the plasmids pEN-1 and pEN-2 are examples of such an expression vector, and contain nucleic acid molecules encoding an HCV NS5 nonstructural region and an unprocessed HCV core antigen-envelope protein, respectively.

For expression, a nucleic acid molecule, typically DNA, as described above is inserted into a suitable vector construct, which in turn is used to transform or transfect appropriate host cells for expression. Preferably, the host cell for use in expressing the gene sequences of the present invention is a prokaryotic host cell, further preferably a bacterium such as *E. coli*. Other suitable host cells include Salmonella, Bacillus, Shigella, Pseudomonas, Streptomyces and other genera known in the art. In a further preferred embodiment, the host cell is an *E. coil* containing a DE3 lysogen or T7 RNA polymerase, such as BL21(DE3), JM109(DE3) or BL21(DE3) pLysS.

Vectors used for expressing cloned DNA sequences in bacterial hosts will generally contain a selectable marker, such as a gene for antibiotic resistance, and a promoter that functions in the host cell. Appropriate promoters include the trp (Nichols and Yanofsky, *Meth. Enzymol.* 101:155–164, 1983), lac (Casadaban et al., *J. Bacteriol.* 143:971–980, 1980), and phage λ (Queen, *J. Mol. Appl. Genet.* 2:1–10, 1983) promoter systems. The expression units may also include a transcriptional terminator. Plasmids useful for transforming bacteria include the pUC plasmids (Messing, *Meth. Enzymol.* 101:20–78, 1983; Vieira and Messing, *Gene* 19:259–268, 1982), pBR322 (Bolivar et al., *Gene* 2:95–113, 1977), pCQV2 (Queen, ibid.), and derivatives thereof. Plasmids may contain both viral and bacterial elements.

In another embodiment, the host cell may be a eukaryotic cell, provided that either the host cell has been modified such that the host cell cannot process, for example, the unprocessed core-like antigen-adjacent protein or unprocessed nonstructural region (such as the NS3-NS4 nonstructural protein), or the processing signals and/or processing sites in the unprocessed polypeptide have been modified such that the protein is no longer susceptible to processing (such modifications should not affect the antigenicity of the unprocessed protein). Eukaryotic host cells suitable for use in practicing the present invention include mammalian, avian, plant, insect and fungal cells. Preferred eukaryotic cells include cultured mammalian cell lines (e.g., rodent or human cell lines), insect cell lines (e.g., Sf-9) and fiungal cells, including species of yeast (e.g., Saccharomyces spp., particularly *S. cerevisiae*, Schizosaccharoniyces spp., or Kluyveromyces spp.) or filamentous fungi (e.g., Aspergillus spp., Neurospora spp.).

Techniques for transforming these host cells, and methods of expressing foreign DNA sequences cloned therein, are well known in the art (see, e.g., Maniatis et al., *Molecular Cloning: A Laboratory Manual,* Cold Spring Harbor Laboratory, 1982; Sambrook et al., supra; "Gene Expression Technology," *Methods in Enzymology,* Vol. 185, Goeddel (ed.), Academic Press, San Diego, Calif., 1990; "Guide to Yeast Genetics and Molecular Biology," *Methods in Enzymology,* Guthrie and Fink (eds.), Academic Press, San Diego, Calif., 1991; Hitzeman et al., *J. Biol. Chem.* 255:12073–12080, 1980; Alber and Kawasaki, *J. Mol. Appl. Genet.* 1:419–434, 1982; Young et al., in *Genetic Engineering of Microorganisms for Chemicals,* Hollaender et al. (eds.), p. 355, Plenum, New York, 1982; Ammerer, *Meth. Enzymol.* 101:192–201, 1983; McKnight et al., U.S. Pat. No. 4,935,349).

In general, a host cell will be selected on the basis of its ability to produce the protein of interest at a high level. In this way, the number of cloned DNA sequences that must be introduced into the host cell can be minimized and overall yield of biologically active protein can be maximized. Given the teachings provided herein, promoters, terminators and methods for introducing such expression vectors encoding the proteins of the present invention into desired host cells would be evident to those of skill in the art.

Host cells containing vector constructs of the present invention are then cultured to express a DNA molecule as described above. The cells are cultured according to standard methods in a culture medium containing nutrients required for growth of the chosen host cells. A variety of suitable media are known in the art and generally include a carbon source, a nitrogen source, essential amino acids, vitamins and minerals, as well as other components, e.g., growth factors or serum, that may be required by the particular host cells. The growth medium will generally select for cells containing the DNA construct(s) by, for example, drug selection or deficiency in an essential nutrient which is complemented by the selectable marker on the DNA construct or co-transfected with the DNA construct.

Polypeptides Comprising the Unprocessed Polypeptides of the Invention

As noted above, the invention provides a polypeptide comprising an unprocessed, substantially complete polyprotein from a positive-stranded RNA virus. The invention also provides a polypeptide comprising a core-like antigen protein, such as the HCV core protein, joined to an amino-terminal portion of an adjacent protein, such as the HCV envelope region. The present invention also provides certain nonstructural proteins. In one preferred embodiment, the amino acid sequence of the core-like antigen protein is that depicted in FIG. 1B (SEQ. ID. No. 8). In such a preferred embodiment, the polypeptide has a molecular weight of about 25,000 daltons as measured by electrophoresis through a sodium dodecyl sulfate-polyacrylamide gel and has been deduced to have about 223 amino acids.

The unprocessed polypeptide from the positive-stranded RNA virus is capable of binding antibodies specific to the positive-stranded RNA virus. In the case of HCV, this has been confirmed by Western Blotting and by enzyme-linked immunosorbent assay (ELISA). The unprocessed core antigen-envelope protein has been found to be specifically reactive with the sera of patients with HCV, and therefore is not reactive with the sera of persons without HCV. The unprocessed polypeptide from the positive-stranded RNA virus is also capable of detecting the presence of antibodies in samples specific to the positive-stranded RNA virus, and therefore is useful for detection and diagnosis of the positive-stranded RNA virus in a patient, particularly a human being.

The present invention also provides a polypeptide comprising a nonstructural protein from the positive-stranded RNA virus. In a preferred embodiment, the polypeptide has the amino acid sequence of the polypeptide given in FIG. 3B (SEQ ID NO. 10). The polypeptide of FIG. 3B (SEQ ID NO. 10) has a molecular weight of about 29,000 daltons as measured by electrophoresis through a sodium dodecyl sulfate-polyacrylamide gel (SDS-PAGE) and has been deduced to have about 267 amino acids.

The nonstructural protein of the present invention is capable of binding antibodies specific to the positive-stranded RNA virus, which in the case of HCV has been confirmed by Western Blotting and (ELISA) for both the NS5 and the NS3-NS4 nonstructural proteins disclosed herein. The nonstructural protein of the present invention is specifically reactive with the sera of patients infected with the positive-stranded RNA virus, and therefore is not reactive with the sera of persons without the positive-stranded RNA virus. The nonstructural protein is also capable of detecting the presence of antibodies specific to the positive-stranded RNA virus in samples, and therefore is useful for diagnosis of the positive-stranded RNA virus in a patient, particularly a human being.

Where the protein of the present invention is encoded by a portion of a native gene, a derivative of a native gene, or has been otherwise modified, the protein maintains substantially the same biological activity of the native protein. For example, the structure of proteins corresponding to the unprocessed, substantially complete polyprotein from a positive-stranded RNA virus, the core-like antigen-adjacent protein, or the nonstructural protein can be predicted from the primary translation products thereof using the hydrophobicity plot function of, for example, P/C Gene or Intelligenetics Suite (Intelligenetics, Mountain View, Calif.), or according to the methods described by Kyte and Doolittle (*J. Mol. Biol.* 157:105–132, 1982).

In a preferred embodiment, the present invention provides isolated proteins. Proteins can be isolated by, among other methods, culturing suitable host and vector systems to produce the recombinant translation products of the present invention. Supernatants from such cell lines, or protein inclusions or whole cells where the protein is not excreted or secreted into the supernatant, can then be treated by a variety of purification procedures in order to isolate the desired proteins. For example, the supernatant may be first concentrated using commercially available protein concentration filters, such as an Amicon or Millipore Pellicon ultrafiltration unit. Following concentration, the concentrate may be applied to a suitable purification matrix such as, for example, an anti-protein antibody bound to a suitable support. Alternatively, anion or cation exchange resins may be employed in order to purify the protein. As a further alternative, one or more reverse-phase high performance liquid chromatography (RP-HPLC) steps may be employed to further purify the protein. Other methods of isolating the proteins of the present invention are well known in the skill of the art. See WO 94/25597 and WO/25598.

A protein is deemed to be "isolated" within the context of the present invention if no other (undesired) protein is detected pursuant to SDS-PAGE analysis followed by coomassie blue staining. Within other embodiments, the desired protein can be isolated such that no other (undesired) protein, and preferably no lipopolysaccharide (LPS), is detected pursuant to SDS-PAGE analysis followed by silver staining. Within still other embodiments, the protein is isolated if no other protein having significant antigenic activity that significantly interferes with detection assays or immunological events is included with the protein.

Antibodies Against the Unprocessed Polypeptides of the Invention

The present invention also provides monoclonal and polyclonal antibodies directed against the unprocessed positive-stranded RNA virus polyprotein, the core-like antigen-adjacent protein of a positive-stranded RNA virus, the nonstructural protein of such positive-stranded RNA virus or other proteins of the invention. The antibodies are produced by using the polypeptide of the invention as an immunogen through standard procedures for preparing a hybridoma, and/or other methods. The resulting antibodies are particularly useful for detecting the positive-stranded RNA virus in a sample, preferably a sample from a human being. See WO 94/25597 and WO/25598.

Polyclonal antibodies can be readily generated by one of ordinary skill in the art from a variety of warm-blooded animals such as horses, cows, goats, sheep, dogs, chickens, turkeys, rabbits, mice, or rats. Briefly, the desired protein or peptide is utilized to immunize the animal, typically through intraperitoneal, intramuscular, intraocular, or subcutaneous injections. The immunogenicity of the protein or peptide of interest may be increased through the use of an adjuvant such as Freund's complete or incomplete adjuvant. Following several booster immunizations, small samples of serum are collected and tested for reactivity to the desired protein or peptide.

Once the titer of the animal has reached a plateau in terms of its reactivity to the protein, larger quantities of polyclonal antisera may be readily obtained either by weekly bleedings, or by exsanguinating the animal.

Monoclonal antibodies can also be readily generated using well-known techniques (see U.S. Pat. Nos. RE 32,011, 4,902,614, 4,543,439, and 4,411,993; see also *Monoclonal Antibodies, Hybridomas: A New Dimension in Biological Analyses,* Plenum Press, Kennett, McKearn, and Bechtol (eds.), 1980, and *Antibodies: A Laboratory Manual,* supra). Briefly, in one embodiment, a subject animal such as a rat or mouse is injected with a desired protein or peptide. If desired, various techniques may be utilized in order to increase the resultant immune response generated by the protein, in order to develop greater antibody reactivity. For example, the desired protein or peptide may be coupled to another protein such as ovalbumin or keyhole limpet hemocyanin (KLH), or through the use of adjuvants such as Freund's complete or incomplete adjuvants. The initial elicitation of an immune response may be through intraperitoneal, intramuscular, intraocular, or subcutaneous routes.

Between one and three weeks after the initial immunization, the animal may be reimmunized with booster immunization. The animal may then be test bled and the serum tested for binding to the unprocessed polypeptide using assays as described above. Additional immunizations may also be accomplished until the animal has reached a plateau in its reactivity to the desired protein or peptide. The animal may then be given a final boost of the desired protein or peptide, and three to four days later sacrificed. At this time, the spleen and lymph nodes may be harvested and disrupted into a single cell suspension by passing the organs through a mesh screen or by rupturing the spleen or lymph node membranes which encapsulate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the protein or peptide of interest that is suitable for generating an immune response as described above. Subsequently, the lymphocytes are harvested and flused as described below.

Cells that are obtained through the use of in vitro immunization or from an immunized animal as described above may be immortalized by transfection with a virus such as the Epstein-Barr Virus (EBV). (See Glasky and Reading, *Hybridoma* 8(4):377–389, 1989.) Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Rockville, Md. (see *Catalogue of Cell Lines & Hybridomas,* 6th ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63-Ag 8.653 (ATCC No. CRL 1580), which may be utilized for fusions with either mouse, rat, or human cell lines. Fusion between the myeloma cell line and the cells from the immunized animal can be accomplished by a variety of methods, including the use of polyethylene glycol (PEG) (see *Antibodies: A Laboratory Manual,* supra) or electrofusion (see Zimmerman and Vienken, *J. Membrane Biol.* 67:165–182, 1982).

Following the fusion, the cells are placed into culture plates containing a suitable medium, such as RPMI 1640 or DMEM (Dulbecco's Modified Eagles Medium, JRH Biosciences, Lenexa, Kan.). The medium may also contain additional ingredients, such as Fetal Bovine Serum (FBS, e.g., from Hyclone, Logan, Utah, or JRH Biosciences), thymocytes that were harvested from a baby animal of the same species as was used for immunization, or agar to solidify the medium. Additionally, the medium should contain a reagent which selectively allows for the growth of fused spleen and myeloma cells. Particularly preferred is the use of HAT medium (hypoxanthine, aminopterin, and thymidine) (Sigma Chemical Co., St. Louis, Mo.). After about seven days, the resulting fused cells or hybridomas may be screened in order to determine the presence of antibodies which recognizes the core-envelope region of said HCV or the HCV nonstructural protein. Following several clonal dilutions and reassays, hybridoma producing antibodies that bind to the protein of interest can be isolated.

Other techniques can also be utilized to construct monoclonal antibodies. (See Huse et al., "Generation of a Large Combinational Library of the Immunoglobulin Repertoire in Phage Lambda," *Science* 246:1275–1281, 1989; see also Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, 1989; see also Alting-Mees et al., "Monoclonal Antibody Expression Libraries: A Rapid Alternative to Hybridomas," *Strategies in Molecular Biology* 3:1–9, 1990; these references describe a commercial system available from Stratacyte, La Jolla, Calif., which enables the production of antibodies through recombinant techniques.) Briefly, mRNA is isolated from a B cell population and utilized to create heavy and light chain immunoglobulin cDNA expression libraries in the λIMMUNOZAP(H) and λIMMUNOZAP(L) vectors. These vectors may be screened individually or co-expressed to form Fab fragments or antibodies (see Huse et al., supra; see also Sastry et al., siipra). Positive plaques can subsequently be converted to a non-lytic plasmid which allows high level expression of monoclonal antibody fragments from *E. coli.*

Similarly, binding partners can also be constructed utilizing recombinant DNA techniques to incorporate the variable regions of a gene that encodes a specifically binding antibody. The construction of these binding partners can be readily accomplished by one of ordinary skill in the art given the disclosure provided herein. (See Larrick et al., "Polymerase Chain Reaction Using Mixed Primers: Cloning of Human Monoclonal Antibody Variable Region Genes From Single Hybridoma Cells,"0 *Biotechnology* 7:934–938, 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to Pseudomonas Exotoxin," *Nature* 339:394–397, 1989; see also U.S. Pat. No. 5,132,405 entitled "Biosynthetic Antibody Binding Sites".) Briefly, in one embodiment, DNA segments encoding the desired protein or peptide interest-specific antigen binding domains are amplified from hybridomas that produce a specifically binding monoclonal antibody, and are inserted directly into the genome of a cell that produces human antibodies. (See Verhoeyen et al., supra; see also Reichmann et al., supra.) This technique allows the antigen-binding, site of a specifically binding mouse or rat monoclonal antibody to be transferred into a human antibody. Such antibodies are preferable for therapeutic use in humans because they are not as antigenic as rat or mouse antibodies.

In an alternative embodiment, genes that encode the variable region from a hybridoma producing a monoclonal antibody of interest are amplified using oligonucleotide primers for the variable region. These primers may be synthesized by one of ordinary skill in the art, or may be purchased from commercially available sources. For instance, primers for mouse and human variable regions including, among others, primers for $V_{Ha}$, $V_{Hb}$, $V_{Hc}$, $V_{Hd}$, $C_{H1}$, $V_L$ and $C_L$ regions, are available from Stratacyte (La Jolla, Calif.). These primers may be utilized to amplify heavy or light chain variable regions, which may then be inserted into vectors such as IMMUNOZAP™(H) or IMMUNOZAP™(L) (Stratacyte), respectively. These vectors may then be introduced into *E. coli* for expression. Utilizing these techniques, large amounts of a single-chain protein containing a fusion of the $V_H$ and $V_L$ domains may be produced (see Bird et al., *Science* 242:423–426, 1988).

Monoclonal antibodies and binding partners can be produced in a number of host systems, including tissue cultures, bacteria, eukaryotic cells, plants and other host systems known in the art.

Once suitable antibodies or binding partners have been obtained, they may be isolated or purified by many techniques well known to those of ordinary skill in the art (see *Antibodies: A Laboratory Manual,* Harlow and Lane (eds.), Cold Spring Harbor Laboratory Press, 1988; U.S. Pat. No. 4,736,110; and U.S. Pat. No. 4,486,530). Suitable isolation techniques include peptide or protein affinity columns, HPLC or RP-BPLC, purification on proteinA or protein G columns, or any combination of these techniques. Within the context of the present invention, the term "isolated" as used to define antibodies or binding partners means "substantially free of other blood components."

The antibodies and binding partners of the present invention have many uses. As discussed further below, the antibodies and binding partners of the present invention are particularly useful for the detection and diagnosis of the positive-stranded RNA virus. Other uses include, for example, flow cytometry to sort cells displaying one more of the proteins of the present invention. Briefly, in order to detect the protein or peptide of interest on cells, the cells are incubated with a labeled monoclonal antibody which specifically binds to the protein of interest, followed by detection of the presence of bound antibody. These steps may also be accomplished with additional steps such as washings to remove unbound antibody. Labels suitable for use within the present invention are well known in the art including, among others, flourescein isothiocyanate (FITC), phycoerythrin (PE), horse radish peroxidase (HRP), and colloidal gold. Particularly preferred for use in flow cytometry is FITC, which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method,"*Immunology* 18:875–881, 1970; Goding, "Conjugation of Antibodies with Fluorochromes: Modification to the Standard Methods," *J. Immunol. Methods* 13:215–226, 1970.)

Assays for the Detection of a Positive-Stranded RNA Virus in a Sample

As noted above, the invention provides a polypeptide comprising an unprocessed, substantially complete polyprotein from a positive-stranded RNA virus. The invention also provides a polypeptide comprising a core-like antigen-adjacent protein and certain nonstructural proteins. The present invention further provides methods for detecting such polypeptides in a sample. The assays are typically based on the detection of antigens displayed by the positive-stranded RNA virus or antibodies produced against the positive-stranded RNA virus, but may also include nucleic acid based assays (typically based upon hybridization), as known in the art. The methods are characterized by the ability of the polypeptides of the present invention to be bound by antibodies against the positive-stranded RNA virus, and the ability of antibodies produced against the proteins of the present invention to bind to antigens of the positive-stranded RNA virus in a sample.

Surprisingly, the unprocessed polypeptides of the present invention provide significantly better and more sensitive detection of the positive-stranded RNA virus. For example, with reference to HCV, the unprocessed core antigen-envelope protein provides significantly better detection of HCV in a sample than processed core protein (sometimes referred to as p22) or fragments of the core protein, alone. Also surprisingly, the use of both an unprocessed core-like antigen-adjacent protein and a nonstructural protein of the positive-stranded RNA virus in the assay provides a synergistic effect that permits significantly more sensitive detection of the positive-stranded RNA virus than when either the unprocessed core-like antigen-adjacent protein or nonstructural protein is utilized alone.

A preferred assay for the detection of the positive-stranded RNA virus is a sandwich assay such as an enzyme-linked immunosorbent assay (ELISA). In one preferred embodiment, the ELISA comprises the following steps: (1) coating a core antigen-envelope protein of the present invention onto a solid phase, (2) incubating a sample suspected of containing HCV antibodies with the polypeptide coated onto the solid phase under conditions that allow the formation of an antigen-antibody complex, (3) adding an anti-antibody (such as anti-IgG) conjugated with a label to be captured by the resulting antigen-antibody complex bound to the solid phase, and (4) measuring the captured label and determining therefrom whether the sample has HCV antibodies.

Although a preferred assay is set forth above, a variety of assays can be utilized in order to detect antibodies that specifically bind to the desired protein from a sample, or to detect the desired protein bound to one or more antibodies from the sample. Exemplary assays are described in detail in *Antibodies: A Laboratory Manual,* Harlow and Lane (eds.), Cold Spring Harbor Laboratory Press, 1988. Representative examples of such assays include: countercurrent immuno-electrophoresis (CIEP), radioimmunoassays, radioimmunoprecipitations, enzyme-linked immunosorbent assays (ELISA), dot blot assays, inhibition or competition assays, sandwich assays, immunostick (dip-stick) assays, simultaneous assays, immunochromatographic assays, immunofiltration assays, latex bead agglutination assays, immunofluorescent assays, biosensor assays, and low-light detection assays (see U.S. Pat. Nos. 4,376,110 and 4,486,530; WO 94/25597; WO/25598; see also *Antibodies: A Laboratory Manual,* supra).

A fluorescent antibody test (FA-test) uses a fluorescently labeled antibody able to bind to one of the proteins of the invention. For detection, visual determinations are made by a technician using fluorescence microscopy, yielding a qualitative result. In one embodiment, this assay is used for the examination of tissue samples or histological sections.

In latex bead agglutination assays, antibodies to one or more of the proteins of the present invention are conjugated to latex beads. The antibodies conjugated to the latex beads are then contacted with a sample under conditions permitting the antibodies to bind to desired proteins in the sample, if any. The results are then read visually, yielding a qualitative result. In one embodiment, this format can be used in the field for on-site testing.

Enzyme immunoassays (EIA) include a number of different assays able to utilize the antibodies provided by the present invention. For example, a heterogeneous indirect EIA uses a solid phase coupled with an antibody of the invention and an affinity purified, anti-IgG immunoglobulin preparation. Preferably, the solid phase is a polystyrene microtiter plate. The antibodies and immunoglobulin preparation are then contacted with the sample under conditions permitting antibody binding, which conditions are well known in the art. The results of such an assay can be read visually, but are preferably read using a spectrophotometer, such as an ELISA plate reader, to yield a quantitative result. An alternative solid phase EIA format includes plastic-coated ferrous metal beads able to be moved during the procedures of the assay by means of a magnet. Yet another alternative is a low-light detection immunoassay format. In this highly sensitive format, the. light emission produced by appropriately labeled bound antibodies are quantitated automatically. Preferably, the reaction is performed using microtiter plates.

In an alternative embodiment, a radioactive tracer is substituted for the enzyme mediated detection in an EIA to produce a radioimmunoassay (RIA).

In a capture-antibody sandwich enzyme assay, the desired protein is bound between an antibody attached to a solid phase, preferably a polystyrene microtiter plate, and a labeled antibody. Preferably, the results are measured using a spectrophotometer, such as an ELISA plate reader. This assay is one preferred embodiment for the present invention.

In a sequential assay format, reagents are allowed to incubate with the capture antibody in a step wise fashion. The test sample is first incubated with the capture antibody. Following a wash step, an incubation with the labeled antibody occurs. In a simultaneous assay, the two incubation periods described in the sequential assay are combined. This eliminates one incubation period plus a wash step.

A dipstick/immunostick format is essentially an immunoassay except that the solid phase, instead of being a polystyrene microtiter plate, is a polystyrene paddle or dipstick. Reagents are the same and the format can either be simultaneous or sequential.

In a chromatographic strip test format, a capture antibody and a labeled antibody are dried onto a chromatographic strip, which is typically nitrocellulose or nylon of high porosity bonded to cellulose acetate. The capture antibody is usually spray dried as a line at one end of the strip. At this end there is an absorbent material that is in contact with the strip. At the other end of the strip the labeled antibody is deposited in a manner that prevents it from being absorbed into the membrane. Usually, the label attached to the antibody is a latex bead or colloidal gold. The assay may be initiated by applying the sample immediately in front of the labeled antibody.

Immunofiltration/immunoconcentration formats combine a large solid phase surface with directional flow of sample/reagents, which concentrates and accelerates the binding of antigen to antibody. In a preferred format, the test sample is preincubated with a labeled antibody then applied to a solid phase such as fiber filters or nitrocellulose membranes or the like. The solid phase can also be precoated with latex or glass beads coated with capture antibody. Detection of analyte is the same as standard immunoassay. The flow of sample/reagents can be modulated by either vacuum or the wicking action of an underlying absorbent material.

A threshold biosensor assay is a sensitive, instrumented assay amenable to screening large numbers of samples at low cost. In one embodiment, such an assay comprises the use of light addressable potentiometric sensors wherein the reaction involves the detection of a pH change due to binding of the desired protein by capture antibodies, bridging antibodies and urease-conjugated antibodies. Upon binding, a pH change is effected that is measurable by translation into electrical potential ($\mu$volts). The assay typically occurs in a very small reaction volume, and is very sensitive. Moreover, the reported detection limit of the assay is 1,000 molecules of urease per minute.

Compositions and Methods for the Elicitation of an Immune Response to HCV

The present invention also provides compositions and methods for the elicitation of an immune response to the positive stranded RNA virus, which be either humoral, cellular, or both. Preferably, the immune response is induced by a vaccine against the positive stranded RNA virus, and is therefore an immunoprotective immune response. These compositions and methods typically involve an immunogen comprising an unprocessed polypeptide of the present invention in combination with a pharmaceutically acceptable carrier or diluent. In a preferred embodiment, the compositions and methods comprise both an unprocessed core antigen-envelope protein of HCV and a nonstructural protein of HCV, further preferably an NS5 nonstructural protein or a NS3-NS4 nonstructural protein. The compositions and methods may also include an inactivated preparation or an attenuated preparation comprising the proteins of the invention.

Accordingly, another aspect of the present invention provides isolated antigens capable of eliciting an immune response, preferably immunogens capable of immunizing an animal. In a preferred embodiment, comprising amino acid sequences or molecules shown in or derived from the sequences shown in FIGS. 1A, 1B, 3A or 3B or substantial equivalents thereof As will be understood by one of ordinary skill in the art, with respect to the polypeptides of the present invention, slight deviations of the amino acid sequences can be made without affecting the immunogenicity of the immunogen. Substantial equivalents of the above proteins include conservative substitutions of amino acids that maintain substantially the same charge and hydrophobicity as the original amino acid. Conservative substitutions include replacement of valine for isoleucine or leucine, and aspartic acid for glutamic acid, as well as other substitutions of a similar nature (See Dayhoff et al. (ed.), "Atlas of Protein Sequence and Structure," *Natl. Biomed. Res. Fdn., 1978*).

As will be evident to one of ordinary skill in the art, the immunogens listed above, including their substantial equivalents, may stimulate different levels of response in different animals. The immunogens listed above, including their substantial equivalents, can be tested for effectiveness as a vaccine. These tests include T-cell proliferation assays, determination of lymphokine production after stimulation, and immunoprotection trials. Briefly, T-cell proliferation assays can be utilized as an indicator of potential for cell-mediated immunity. Additionally, evidence of lymphokine production after stimulation by an immunogen can be utilized to determine the potential for protection provided by an immunogen.

Finally, as described below, actual immunoprotection trials can be performed in order to determine protection in animals. In the case of humans, however, instead of immunoprotection trials it is preferred to first screen peripheral blood lymphocytes (PBLs) from patients infected with HCV in the following manner. Briefly, PBLs can be isolated from diluted whole blood using Ficoll density gradient centrifugation and utilized in cell proliferation studies with [$^3$H]-thymidine as described below. Positive peptides are then selected and utilized in primate trials.

The immunogens, or polypeptides, of the present invention can be readily produced utilizing many other techniques well known in the art (see Sambrook et al., supra, *Molecular Cloning, A Laboratory Manual*, Cold Spring Harbor Laboratory Press, 1989).

The immunogens comprising a polypeptides of the present invention in combination with a pharmaceutically acceptable carrier or diluent can be administered to a patient in accordance with a number procedures known in the art See WO 94/25597 and WO/25598.

For purposes of the present invention, warm-blooded animals include, among others, humans and primates.

Many suitable carriers or diluents can be utilized in the present invention, including among others saline, buffered saline, and saline mixed with nonspecific serum albumin. The pharmaceutical composition may also contain other excipient ingredients, including adjuvants, buffers, antioxidants, carbohydrates such as glucose, sucrose, or dextrins, and chelating agents such as EDTA. Within a particularly preferred embodiment, an adjuvant is utilized along with the immunogen. Example of such adjuvants include alum or aluminum hydroxide for humans.

The amount and frequency of administration can be determined in clinical trials, and may depend upon such factors as the positive stranded RNA viral species against which it is desired to protect, the particular antigen used, the degree of protection required, and many other factors. In a preferred embodiment, immunizations will involve oral administration. Alternatively, the vaccine can be parenterally administered via the subcutaneous route, or via other routes. Depending upon the application, quantities of injected immunogen will vary from 50 $\mu$g to several milligrams in an adjuvant vehicle and preferably about 100 $\mu$g to 1 mg, in combination with a physiologically acceptable carrier or diluent. Booster immunizations can be given from 4–6 weeks later.

The present invention also includes the administration of a nucleic acid vector capable of expressing the unprocessed core antigen-envelope protein or nonstructural protein of HCV (or both) into an animal, wherein the nucleic acid molecule can elicit an immune response in, and preferably immunize, an animal against the expressed protein expressed from the nucleic molecule, and therefore HCV. In one embodiment of this procedure, naked DNA is introduced into an appropriate cell, such as a muscle cell, where it produces protein that is then displayed on the surface of the cell, thereby eliciting a response from host cytotoxic T-lymphocytes (CTLs). This can provide an advantage over traditional immunogens wherein the elicited response comprises specific antibodies. Specific antibodies are generally strain-specific and cannot recognize the corresponding antigen on a different strain. CTLs, on the other hand, are specific for conserved antigens and can respond to different strains expressing a corresponding antigen (Ulmer et al., "Heterologous protection against influenza by injection of DNA encoding a viral protein," *Science* 259:1745–1749, 1993; Lin et al., "Expression of recombinant genes in myocardium in vivo after direct injection of DNA," *Circulation* 82:2217–21, 1990); Wolff et al., "Long-term persistence of plasma DNA and foreign gene expression in mouse muscle," *Human Mol. Gen.* 1:363–69, 1992)

Upon introduction of the naked vector construct into the animal's cell, the construct is then able to express the nucleic acid molecule (typically a gene) that it carries, which gene preferably comprises one (or more) of the unprocessed core antigen-envelope protein or nonstructural protein of HCV. Accordingly, upon expression of the desired peptide, an immune response is elicited from the host animal. Preferably, the immune response includes $CD8^+$ CTLs able to respond to different strains that exhibit a form of the desired peptide.

Kits for the Implementation of the Various Aspects of the Claimed Invention

The present invention further provides kits for analyzing samples for the presence of antigens or antibodies from the positive-stranded RNA virus. The kits comprises a polypeptide or antibody of the invention and an appropriate solid phase. Preferably, the polypeptide is bound to the solid phase.

The present invention also provides kits for the induction of an immune response. The kits comprise compositions comprising a polypeptide of the invention in combination with an pharmaceutically acceptable carrier or diluent, with means for administering or assisting in the administration of the composition.

Other kits suitable for use with the features of the present invention are also provided herewith.

The following Examples are offered by way of illustration, and not by way of limitation.

EXAMPLES

The following examples are separated into three groupings. First, are Examples relating to the isolation and production of a suitable core-like antigen-adjacent protein, namely an HCV unprocessed core antigen-envelope fusion protein, and uses thereof without a nonstructural protein. Second, are Examples relating to the isolation and production of an appropriate second protein for use with the core-like antigen-adjacent protein, namely an HCV nonstructural protein, and uses thereof without the HCV core antigen-envelope ftision protein. Third, are Examples relating to the combination and use of the core-like antigen-adjacent protein with second proteins selected from an HCV NS5 protein, an HCV NS3-NS4 protein, an HIV envelope protein and an HTLV-I envelope protein.

THE ISOLATION AND PRODUCTION OF A CORE-LIKE ANTIGEN-ADJACENT PROTEIN

1. Cloning of an HCV cDNA

The plasma of patients infected with the Hepatitis C virus was collected and ultracentrifuiged at 4° C. and then the viral particles were obtained. Viral nucleic acid (RNA) was then extracted and purified from the viral particles using guanidine isothiocyanate and acidic phenol (Chomczynski et al., *Anal. Biochem.* 162:156–159, 1987).

The following oligonucleotide sequences:

(i) 5'-GGATCCATGAGCACAAATCCTAAA CCT-3' (SEQ ID NO. 1)

and (ii) 5'-GAATTCGGTGTGCATGATCATGTC CGC-3' (SEQ ID NO. 2)

were used as primers in the cloning of cDNA. A single-stranded DNA molecule was produced using random primers, reverse transcriptase, and the RNA template. The double-stranded DNA molecule containing the HCV core-envelope region sequence was amplified by the PCR method using Taq polymerase and primers (i) and (ii).

The cloned DNA molecule was subjected to sequence analysis for identification. The obtained molecule was designated EN-80-2. The DNA sequence of the molecule EN-80-2 is given in FIG. 1A (SEQ ID NO: 7). The DNA molecule was derived from the HCV core and envelope regions and has 669 bp.

2. Construction of a Plasmid Containing an HCV cDNA

The molecule EN-80-2 was treated with restriction endonucleases Bam HI and EcoRI to obtain a DNA fragment containing the desired HCV cDNA. The obtained DNA fragment was inserted into a vehicle plasmid which had been first cleaved with the restriction endonucleases Bam HI and EcoRI, to obtain an expression plasmid, designated pEN-2. The expression of the HCV cDNA is under the control of a T7 promoter. The structure of the expression plasmid pEN-2 and a restriction map are depicted in FIG. 2.

3. Transformation of *E. coli*

The expression plasmid pEN-2 were transformed into *E. Coli* BL21 (DE3), spread into an ampicillin-agar plate and placed in a 37° C. incubator overnight. *E. coli* colonies producing HCV core antigen protein were selected by screening their expression products by SDA-PAGE and Western Blotting.

4. Production of the Unprocessed Core Antigen-Envelope Protein

The transformed *E. coli* colonies were incubated in a conditioned culture medium. The colonies were centrifu,ged and lysed by freezing-thawing cycles and lysozyme-digestion. The unprocessed core antigen-envelope protein product was released by the lysed cells and purified by column chromatography. The polypeptide was more than 90% pure.

The unprocessed core antigen-envelope protein has a molecular weight of about 25,000 daltons as measured by electrophoresis through a sodium dodecyl sulfate-polyacrylamide gel.

5. Immunological Reactivity of HCV Core Antigen With HCV Antibodies by Western Blotting The purified unprocessed core antigen-envelope protein was subjected to an SDS-PAGE electrophoresis using standard procedures. The SDS-PAGE gel was washed with deionized water at 4° C. for 15 minutes and washed with Blotting Buffer (0.15M sodium phosphate buffer, pH 6.7) at 4° C. for 20 minutes. The polypeptide on the gel was then electroblotted onto nitrocellulose membrane under the Blotting Buffer at 1.3 A for 1–1.5 hours. The membrane was washed with Wash Buffer (PBS-Tween 20, pH 7.4) and blocked with Blocking Buffer (0.1M NaCl, 5 mM EDTA, 50 mM Tris, pH 7.2–7.4, 0.2% bovine serum albumin, 0.05% Nonidet p-40, 1M urea) overnight.

The membrane was reacted with the sera of the persons infected with/without hepatitis C, which were first diluted with 40% Newborn Bovine Serum/Tris-HCl (pH 7.4), 10×, at 40° C. for 2 hours. After the reaction, the membrane was washed with Wash Buffer three times. The membrane was reacted with an anti-hIgG:HRPO conjugate (which was prepared as described hereafter) at 40° C. for 2 hours. After the reaction, the membrane was washed with Wash Buffer three times and then reacted with 10 ml Substrate Solution (0.01% 4-chloro-1-naphthol, 18% methanol, 0.04M Tris, pH 7.2–7.4, 0.1M NaCl and 0.01% $H_2O_2$) for 20 minutes. The unprocessed core antigen-envelope protein of the present invention was reactive with the sera of HCV patients but not reactive with the sera of healthy persons.

6. ELISA for HCV Antibodies (A) Treatment of Microtiter Plate

A microtiter plate was coated with the purified unprocessed core antigen-envelope protein of the invention at appropriate concentrations and blocked with a buffer containing bovine serum albumin. The treated microtiter plate was stored at 2–8° C.

(B) Preparation of Anti-hIgG:HRPO Conjugate

Purified anti-human Immunoglobulin G (anti-hIgG) was conjugated with horse radish peroxidase (HRPO) using $NaIO_4$ to obtain the anti-IgG:HRPO conjugate. The conjugate was purified by chromatography.

(C) Components of Reagents
   (a) Wash Solution: Phosphate Buffer containing 0.9% NaCl and Thimerosal.
   (b) Anti-hIgG:HRPO Conjugate Solution: the anti-hIgG:HRPO conjugate prepared as described above dissolved in Tris Buffer containing a proteineous stabilizer and antiseptics.
   (c) Sample Diluent: Tris Buffer containing a proteineous stabilizer and antiseptics.
   (d) OPD Substrate Solution: o-phenylene diamine (OPD) dissolved in citrate-phosphate buffer containing $H_2O_2$. (If the solution becomes orange, it means that the solution has been contaminated and cannot be used any more.)
   (e) Stopping Solution: 2N $H_2SO_4$ solution.
   (f) Positive/Negative controls: the serum samples of persons infected with/without hepatitis C diluted with phosphate buffer containing a proteineous stabilizer and antiseptics at an appropriate concentration.

(D) Procedure
   (a) One hundred and fifty microliters ($\mu l$) of the test samples were diluted with Sample Diluent (1:10), and Positive/Negative Controls were added into the wells of the treated microtiter plate. Some wells were retained as substrate blanks.
   (b) The plate was gently mixed by shaking and incubated at 37–40° C. for 1 hour.
   (c) The plate was washed three times with 0.3 ml of Wash solution per well.
   (d) One hundred $\mu l$ of anti-hIgG:HRPO Conjugate Solution was added to each well.
   (e) The plate was gently mixed by shaking and incubated at 37–40° C. for 30 minutes.
   (f) The plate was washed five times.
   (g) One hundred $\mu l$ of OPD Substrate Solution was added to each well and the plate was incubated at 15–30° C. in the dark for 30 minutes.
   (h) One hundred $\mu l$ of Stopping Solution was added to each well and gently mixed to stop the reaction.
   (i) The OD value per well was measured at 492 nm in a spectrophotometer.

(E) Determination

The $OD_{492nm}$ value per well subtracts the mean of the readings of the blanks (backgrounds). The difference (PCx-NCx) between the mean of the readings of the positive controls (PCx) and that of the negative controls (NCx) is equal to or more than 0.5.

The Cut-off value (CO) is calculated by the following formula:

$$CO = PCx \times 0.15 + NCx$$

When the readings from test samples were less than the CO value, the samples were considered negative (i.e., HCV antibodies could not be detected in the samples).

When the readings of test samples were equal to or more than the CO value, the samples were expected to be positive; however, it is preferred to repeat the assay for the samples in duplicate. If the readings of either of the duplicate samples were less than the CO value, the samples were considered to be negative. If the duplicate samples were both more than or equal to the Cut-off value, the samples were considered to be positive.

When the readings of test samples are more than NCx but less than the CO value by 20%, the samples should be regarded as questionable samples and the assay has to be repeated for those samples.

Twenty-seven samples were tested by the ELISA according to the invention. At the same time, the samples were also tested with the Abbott's kit (II) HCV antibody assay, which kit contains both structural and nonstructural proteins (i.e., core (amino acids: 1–150), NS-3 and NS-4). The comparison between the test results of Abbott's kit (II) and those of the assay of the present invention is given in Table 1. It is noted that the results of Sample G 229 were negative according to Abbott's kit (II), but were positive according to the assay of the present invention. Sample G 229 was confirmed to be positive for HCV.

TABLE 1

| Sample No. | | $OD_{492\ nm}$ | Results | References Abbott's kit (II) |
|---|---|---|---|---|
| TSGH | 56 | >2.0 | positive | positive |
| TSGH | 57 | >2.0 | positive | positive |
| G | 23 | 1.469 | positive | positive |
| G | 30 | >2.0 | positive | positive |
| G | 32 | >2.0 | positive | positive |
| G | 49 | >2.0 | positive | positive |
| G | 56 | >2.0 | positive | positive |
| G | 58 | >2.0 | positive | positive |
| G | 114 | 1.559 | positive | positive |
| G | 128 | >2.0 | positive | positive |

TABLE 1-continued

| Sample No. | | $OD_{492\ nm}$ | Results | References Abbott's kit (II) |
|---|---|---|---|---|
| G | 186 | >2.0 | positive | positive |
| G | 208 | >2.0 | positive | positive |
| G | 214 | >2.0 | positive | positive |
| G | 231 | >2.0 | positive | positive |
| G | 250 | >2.0 | positive | positive |
| Y | 1 | >2.0 | positive | positive |
| USB | 9 | >2.0 | positive | positive |
| USB | 19 | >2.0 | positive | positive |
| USB | 20 | >2.0 | positive | positive |
| USB | 23 | 0.952 | positive | positive |
| USB | 27 | 0.753 | positive | positive |
| G | 11 | 0.147 | negative | negative |
| G | 12 | 0.077 | negative | negative |
| G | 13 | 0.061 | negative | negative |
| G | 14 | 0.116 | negative | negative |
| G | 15 | 0.139 | negative | negative |
| G | 229 | 0.517 | positive | negative |

THE ISOLATION AND PRODUCTION OF A SUITABLE SECOND PROTEIN, AN HCV NONSTRUCTURAL PROTEIN

7. Cloning of an HCV cDNA Encoding The NS5 Nonstructural Protein

The plasma of patients infected with Hepatitis C virus was collected and ultracentrifuged at 4° C. and then the viral particles were obtained. Subsequently, the viral nucleic acid (RNA) was extracted and purified from the viral particles using guanidine isothiocyanate and acidic phenol (Chomczynski et al., *Anal. Biochem.* 162:156–159, 1987).

(i) 5'-GGATCCCGGTGGAGGATGAGAGGG
    AAATATCCG-3' (SEQ ID NO. 3)

and (ii) 5'-GAATTCCCGGACGTCCTTCGCCCCGTAGCCAAATTT-
    3' (SEQ ID NO. 4)

were used as primers in the cloning of cDNA. A single-stranded DNA molecule was produced using random primers, reverse transcriptase, and the RNA template. The double-stranded DNA molecule containing the NS-5 sequence was amplified by the PCR method using Taq polymerase and primers (i) and (ii).

The cloned DNA molecule was subjected to sequence analysis for identification. The obtained molecule was designated EN-80-1. The DNA sequence of the molecule EN-80-1 is given in FIG. 3A, and the amino acid sequence encoded by the molecule is given in FIG. 3B. The DNA molecule was derived from the genome of HCV nonstructural region 5 and has 803 bp. The amino acid sequence of the molecule EN-80-1 is given in FIG. 3B (SEQ ID NO. 9), and has 267 residues.

8. Construction of a Plasmid Containing an HCV cDNA

The molecule EN-80-1 was treated with restriction endonucleases Bam HI and EcoRI to obtain a DNA fragment containing said HCV cDNA. The resulting DNA fragment was inserted into a vehicle plasmid which had been first cleaved with restriction endonucleases Bam HI and EcoRI, to obtain an expression plasmid, designated pEN-1. The expression of the HCV cDNA is under the control of a T7 promoter. The structure of the expression plasmid pEN-1 and restriction map are given in FIG. 4.

9. Transformation of *E. coli*

The expression plasmid pEN-1 were transformed into *E. coli* BL21 (DE3), spread onto an ampicillin-agar plate and placed at 37° C. incubator for overnight. *E. coli* colonies producing the HCV nonstructural protein were selected by screening their expression products by SDS-PAGE and Western Blotting.

10. Production of The NS5 Nonstructural Protein

The transformed *E. coli* colonies were incubated in a conditioned culture medium. The colonies were centrifuged and lysed by freezing-thawing cycles and lysozyme-digestion. The protein product was released by the lysed cells and purified by column chromatography. The resulting polypeptide was more than 90% pure.

The polypeptide has a molecular weight of about 29,000 daltons as measured by electrophoresis through a sodium dodecyl sulfate-polyacrylamide gel.

11. Immunological Reactivity of the NS5 Nonstructural Protein with HCV Antibodies by Western Blotting The purified polypeptide was subjected to SDS-polyacrylamide gel electrophoresis using standard procedures. The SDS-PAGE gel was washed with deionized water at 4° C. for 15 minutes and washed with Blotting Buffer (0.15M sodium phosphate buffer, pH 6.7) at 4° C. for 20 minutes. The polypeptide on the gel was then electroblotted onto a nitrocellulose membrane under the Blotting Buffer at 1.3A for 1–1.5 hours. The membrane was washed with Wash Buffer (PBS-Tween 20, pH 7.4) and blocked with Blocking Buffer (0.1M NaCl, 5 mM EDTA, 50 mM Tris, pH 7.2–7.4, 0.2% bovine serum albumin, 0.05% Nonidet p-40, 1M urea) overnight.

The membrane was reacted with the sera of the persons infected with/without hepatitis C, which were first diluted with 40% Newborn Bovine Serun/Tris-HCl (pH 7.4), 10×, at 40° C. for 2 hours. After the reaction, the membrane was washed with Wash Buffer three times. The membrane was then reacted with an anti-hIgG:HRPO conjugate (which is prepared as described hereafter) at 40° C. for 2 hours. After the reaction, the paper was washed with Wash Buffer three times and then reacted with 10 ml Substrate Solution (0.01% 4-chloro-1-naphthol, 18% methanol, 0.04M Tris, pH 7.2–7.4, 0.1M NaCl and 0.01% $H_2O_2$) for 20 minutes. The polypeptide of the present invention was reactive with the sera of HCV patients but was not reactive with the sera of healthy persons.

12. ELISA for HCV Antibodies (A) Treatment of Microtiter Plate

A microtiter plate was coated with the NS5 nonstructural protein of the invention at appropriate concentrations and blocked with a buffer containing bovine serum albumin. The treated microtiter plate was stored at 2–8° C.

(B) Preparation of Anti-hIgG:HRPO Conjugate

The purified anti-human Immunoglobulin G (anti-hIgG) was conjugated with horse radish peroxidase (HRPO) using $NaIO_4$ to obtain the anti-IgG:HRPO conjugate. The conjugate was purified by chromatography.

(C) Components of Reagents
  (a) Wash Solution: Phosphate Buffer containing 0.9% NaCl and Thimerosal.
  (b) Anti-hIgG:HRPO Conjugate Solution: the anti-hIgG:HRPO conjugate prepared as described above dissolved in Tris Buffer containing a proteineous stabilizer and antiseptics.
  (c) Sample Diluent: Tris Buffer containing a proteineous stabilizer and antiseptics.
  (d) OPD Substrate Solution: o-phenylene diamine (OPD) dissolved in citrate-phosphate buffer containing $H_2O_2$. (If the solution becomes orange, it means that the solution has been contaminated and cannot be used any more.)
  (e) Stopping Solution: 2N $H_2SO_4$ solution.
  (f) Positive/Negative controls: the serum samples of persons infected with/without hepatitis C diluted with phosphate buffer containing a proteineous stabilizer and antiseptics at an appropriate concentration.

(D) Procedure (a) One hundred and fifty microliters (μl) of test samples diluted with Sample Diluent (1:10) and Positive/Negative Controls were added to the wells of the treated microtiter plate. Some wells were retained as substrate blanks.

(b) The plate was gently mixed by shaking and incubated at 37–40° C. for 1 hour.

(c) The plate was washed three times with 0.3 μl of Wash Solution per well.

(d) One hundred μl of anti-hIgG:HRPO Conjugate Solution was added to each well.

(e) The plate was gently mixed and incubated by shaking at 37–40° C. for 30 minutes.

(f) The plate was washed five times.

(g) One hundred μl of OPD Substrate Solution was added to each well and the plate was incubated at 15–30° C. in the dark for 30 minutes.

(h) One hundred μl of Stopping Solution was added to each well and gently mixed to stop the reaction.

(i) The OD value per well was measured at 492 nm in a spectrophotometer.

(E) Determination

The $OD_{492nm}$ value per well subtracts the mean of the readings of the blanks (backgrounds). The difference (PCx-NCx) between the mean of the readings of the positive controls (PCx) and that of the negative controls (NCx) is equal to or more than 0.5.

The Cut-off value (CO) is calculated by the following formula:

$$CO = PCx \times 0.15 + NCx$$

When the readings of test samples were less than the CO value, the samples were considered to be negative (i.e., HCV antibodies could not be detected in the samples). When the readings of test samples were equal to or more than the CO value, the samples were expected to be positive; however, it is preferred to repeat the assay for the samples in duplicate. If the readings of either of the duplicate samples were less than the CO value, the samples will be negative. If the duplicate samples were both more than or equal to the CO value, the samples were considered to be positive.

When the readings of the test samples are more than NCx but less than the CO value by 20%, the samples should be regarded as questionable samples and the assay has to be repeated for the samples.

Eighteen samples were tested by the ELISA according to the invention. At the same time, the samples were also tested with the Abbott's kit (I) HCV antibody assay, which kit contains the nonstructural protein C100–3, and with the Abbott's kit (II) HCV antibody assay, which kit contains both structural and nonstructural proteins. The comparison between the test results of the Abbott's kits and those-of the assay of the invention is given in Table 2. It is noted that the results of Sample G 30 and Sample G 128 were negative according to Abbott's kit (I) but were positive according to the assay of the present invention. These samples were confirmed to be positive for HCV.

TABLE 2

| Sample No. | $OD_{492\ nm}$ | Results | References Abbott's kit (I) | (II) |
|---|---|---|---|---|
| TSGH | 56 | >2.0 | positive | positive | positive |
| G | 23 | 0.813 | positive | positive | positive |
| G | 26 | 1.607 | positive | positive | positive |
| G | 30 | >2.0 | positive | negative | positive |
| G | 32 | >2.0 | positive | positive | positive |
| G | 56 | >2.0 | positive | positive | positive |
| G | 128 | >2.0 | positive | negative | positive |
| G | 186 | >2.0 | positive | positive | positive |
| G | 208 | >2.0 | positive | — | positive |
| G | 214 | >2.0 | positive | — | positive |
| G | 231 | >2.0 | positive | — | positive |
| Y | 1 | >2.0 | positive | — | positive |
| USB | 9 | >2.0 | positive | — | positive |
| USB | 19 | >2.0 | positive | — | positive |
| USB | 20 | >2.0 | positive | — | positive |
| G | 201 | 0.062 | negative | — | negative |
| G | 202 | 0.072 | negative | — | negative |
| G | 211 | 0.059 | negative | — | negative |

DETECTION USING BOTH A CORE-LIKE ANTIGEN-ADJACENT PROTEIN AND A SECOND PROTEIN

13. ELISAs for HCV Using Both Unprocessed Core Antigen-Envelope Protein and an NS5 Nonstructural Protein A. Assays Comparing the Core Antigen-envelope Protein and the NS5 Nonstructural Protein with Abbott's HCV Assays I. First Assay The method was analogous to the ELISAs described above, except that unprocessed core antigen-envelope protein was combined with an NS5 nonstructural protein (9:1) (known as the EverNew Anti-HCV EIA).

In a first assay, twenty-four samples were tested by the above-described method. At the same time, the samples were also tested by Abbott's kit (II). The results are given in Table 3. In this assay, the results of the Abbott's kit (II) were the same as the assay using the antigens of the present invention.

TABLE 3

| Sample No. | $OD_{492\ nm}$ | Results | References Abbott's kit (II) |
|---|---|---|---|
| TSGH | 56 | >2.0 | positive | positive |
| TSGH | 57 | >2.0 | positive | positive |
| G | 23 | 1.469 | positive | positive |
| G | 26 | >2.0 | positive | positive |
| G | 30 | >2.0 | positive | positive |
| G | 32 | >2.0 | positive | positive |
| G | 49 | >2.0 | positive | positive |
| G | 56 | >2.0 | positive | positive |
| G | 58 | >2.0 | positive | positive |
| G | 114 | >2.0 | positive | positive |
| G | 128 | >2.0 | positive | positive |
| G | 186 | >2.0 | positive | positive |
| G | 214 | >2.0 | positive | positive |
| G | 231 | >2.0 | positive | positive |
| G | 250 | >2.0 | positive | positive |
| Y | 1 | >2.0 | positive | positive |
| USB | 9 | >2.0 | positive | positive |
| USB | 19 | >2.0 | positive | positive |
| USB | 20 | >2.0 | positive | positive |
| USB | 23 | >2.0 | positive | positive |
| USB | 27 | >2.0 | positive | positive |
| G | 92 | 0.038 | negative | negative |

TABLE 3-continued

| Sample No. | | OD$_{492\ nm}$ | Results | References Abbott's kit (II) |
|---|---|---|---|---|
| G | 93 | 0.056 | negative | negative |
| G | 94 | 0.071 | negative | negative |

II. Second Assay

The clinical trial report of blood donors for EverNew Anti-HCV EIA is shown in TABLE 4:

Hospital: Taipei Tri-Service General Hospital
Sample Source: Collected from Blood Bank
Classification of Sample: Volunteer Blood Donors
Reference Kit: Abbott's Kit (II)
Results:

TABLE 4

| | | ABBOTT | | |
|---|---|---|---|---|
| | | + | − | Total |
| EverNew | + | 5 (2.5%) | 1 (0.5%) | 6 (3%) |
| | − | 1 (0.5%) | 193 (96.5%) | 194 (97%) |
| | total | 6 (3%) | 194 (97%) | 200 (100%) |

The results in Table 4 indicate that both assays provided the same detection.

III. Third Assay

The clinical trial report of high risk patients for EverNew Anti-HCV EIA is shown in TABLE 5:

Hospital: Taipei Veteran General Hospital
Sample Source: Collected from Department of Clinical Virology
Classification:

| NANB, sporadic | 20 |
|---|---|
| NANB, PHT | 12 |
| HCC | 15 |
| Liver cirrhosis | 9 |
| Chronic hepatitis B and carrier | 10 |
| Biliary tract stones | 4 |
| Alcoholic liver disease | 3 |
| Fatty liver | 2 |
| Acute hepatitis, etiology? | 2 |
| Schistosomiasis of liver | 1 |
| Hepatic cysts | 1 |
| Cholangio-CA | 1 |
| Non-hepatobiliary disease | 6 |
| No data | 2 |
| Total | 88 |

Reference Kit: ABBOTT HCV EIA 2nd generation
Results:

TABLE 5

| | | ABBOTT | | |
|---|---|---|---|---|
| | | + | − | Total |
| EverNew | + | 54 (61.36%) | 0 (0%) | 54 (61.36%) |
| | − | 1 (1.14%)@ | 33 (37.5%) | 34 (38.64%) |
| | total | 55 (62.5%) | 33 (37.5%) | 88 (100%) |

@: HCV RT/PCR Method: Negative

The clinical data and the HCV RT/PCR results indicate that the efficiency of the EverNew Anti-HCV EIA for HCV antibody detection was better than the ABBOTT HCV EIA 2nd generation licensed by the U.S. FDA.

B. Assays Showing the Synergistic Cooperation of the Core Antigen-envelope Protein and a Second Protein, Including and HCV NS5 Nonstructural Protein, an HCV NS3-NS4 Nonstructural Protein, an HIV Envelope Protein and an HTLV-I Envelope Protein I. First Assay This assay shows the results of an ELISA similar to those set forth above, and shows cooperative interaction between EN-80-2 and EN-80-1 proteins of HCV. The protocol for the ELISA is as follows:

Coating buffer: 0.05 M Tris-HCl/0.15N NaCl/6 M Urea pH: 7.4±0.2.

Washing buffer: PBS with 0.05% Tween 20.

Postcoating buffer: PBS buffer with 1% BSA.

Coating procedure: EN-80-1 and EN-80-2 proteins were added into coating buffer (final concentration: about 1.5 μg/ml) and mixed at room temperature for 30 minutes. After mixing, the diluted EN-80-1 and EN-80-2 proteins were added into microtiter wells, 100 μl/well, and incubated in a 40° C. incubator for 24 hours. The microtiter wells were then washed, and postcoating buffer was added into wells. The microtiter wells were then let stand at 4° C. for overnight. After postcoating, the coated microtiter wells can be used for anti-HCV antibody detection.

Sample diluent: 0.1M Tris-HCl pH: 7.4±0.2 with 40% NBBS, 1% BSA and 2% mouse serum.

Conjugate: anti-human IgG monoclonal antibody coupled with HRPO using NaIO$_4$. After coupling, the anti-human IgG:HRPO conjugates were purified by S-200 gel filtration and were diluted in sample diluent.

OPD tablets: purchased from Beckman.

Substrate diluent: citrate-phosphate buffer containing H$_2$O$_2$.

Stopping Solution: 2N H$_2$SO$_4$.

Positive control: anti-HCV positive serum diluted in sample diluent.

Negative control: recalcified human serum, which is nonreactive for HBV markers, anti-HIV, anti-HTLV I and anti-HCV.

Assay procedure:

100 μl sample diluent was added into each well.

50 μl sample, positive control and negative control was added into appropriate wells.

Sample incubation: incubated at 40±1° C. for 30±2 minutes.

Sample wash: the wells were washed 3 times using washing buffer.

100 μl anti-human IgG:HRPO conjugate was added into each well.

Conjugate incubation: incubated at 40±1° C. for 30±2 minutes.

Conjugate wash: the wells were washed 6 times using washing buffer.

After washing, 100 μl substrate solution was added (the substrate solution was prepared by dissolving one tablet OPD in 5 ml substrate diluent), then the mixture was allowed to stand at room temperature for 10 minutes. In order to prevent light, the microtiter wells were covered with a black cover.

100 μl stopping solution was added into each well. Gently mix.

Evaluation: The OD value per well was measured at 492 nm in a spectrophotometer.

Interpretation:

Determination of cutoff value: cutoff value=PCx×0.25+NCx.

An absorbance equal to or greater than cutoff value indicated that a reaction was considered to be positive, which means reactive for anti-HCV antibody. An absorbance less than the cutoff value was considered to be negative, which means non-reactive for anti-HCV antibody.

The sample sources for the assay reflected in Table 6 were as follows:

Sample source I: G83, G191, G205 and G235 were GPT abnormal samples that were anti-HCV antibody negative and were collected from Taipei blood donation center.

Sample source II: G614 and G615 were anti-HCV antibody positive and were purchased from the U.S.A.

Sample source III: 8-5 was anti-HCV antibody positive and was collected from the Taichung blood donation center.

Sample source IV: N345 was a patient serum.

TABLE 6

| Sample | | EN-80-1 | EN-80-2 | EN-80-1 + EN-80-2 |
|---|---|---|---|---|
| G83 | | 0.027@ | 0.047 | 0.055 |
| G191 | | 0.071 | 0.209 | 0.056 |
| G205 | | 0.027 | 0.034 | 0.039 |
| G235 | | 0.025 | 0.044 | 0.043 |
| G614 | 8×# | 0.066 | 0.831 | 1.894 |
| G614 | 16× | 0.059 | 0.348 | 0.848 |
| G615 | 8× | 0.048 | 0.495 | 1.592 |
| G615 | 16× | 0.053 | 0.209 | 0.740 |
| 8-5 | | 0.059 | 0.352 | 0.690 |
| N345$ | | 0.008 | 0.420 | 0.730 |

@: Absorbance at 492 nm.
: Samples were diluted with recalcified human serum which is non-reactive for HBV, HCV and HIV.
$: Abbott's kit (II) found this sample to be negative.

These data demonstrate that when the EN-80-2 and EN-80-1 proteins were combined, the absorbance at 492 nm for anti-HCV positive samples was synergistic, not additive. Thus, cooperative interactions between EN-80-2 and EN-80-1 proteins of HCV were found. One benefit of this synergism is shown, for example, with sample N345, which was found to be HCV negative by Abbott's kit (II), but due to the synergistic effect was found to be positive by the present invention. These data also demonstrate that the synergistic effect is helpful in screening for anti-HCV antibodies in samples, particularly in early detection situations.

II. Second Assay

This assay was conducted as set forth in the First Assay, above, and included the provision in a single well of a core-envelope fusion protein of the invention in combination with an NS3-NS4 protein identified as EN-80-4. The results of the ELISA are set forth in Table 7.

TABLE 7

| Sample | | EN-80-2 | EN-80-4 | EN-80-2 + EN-80-4 |
|---|---|---|---|---|
| G83 | | 0.047@ | 0.032 | 0.049 |
| G191 | | 0.209 | 0.103 | 0.102 |

TABLE 7-continued

| Sample | | EN-80-2 | EN-80-4 | EN-80-2 + EN-80-4 |
|---|---|---|---|---|
| G205 | | 0.034 | 0.045 | 0.046 |
| G235 | | 0.044 | 0.064 | 0.068 |
| G58 | 21×# | 0.561 | 0.041 | 1.729 |
| G612 | 161× | 1.298 | 0.218 | >2.0 |
| G613 | 40× | 0.202 | 0.243 | 0.708 |

@: Absorbance at 492 nm.
: Samples were diluted with recalcified human serum, which is non-reactive for HBV, HCV and HIV.

The data in Table 7 demonstrate that when the EN-80-2 and EN-80-4 proteins were combined, the absorbance at 492 nm for anti-HCV positive samples showed a synergistic effect, not merely an additive effect. Thus, cooperative interactions between EN-80-2 and EN-80-4 proteins of HCV were found.

III. Third Assay

This assay was conducted as set forth in the First Assay, above, and included the provision in a single well of a core-envelope fusion protein of the invention in combination with an HIV envelope protein. The results of the ELISA are set forth in Table 8.

TABLE 8

| Samples | | EN-80-2 | HIV envelope | EN-80-2 + HIV envelope |
|---|---|---|---|---|
| Recalcified human serum | | 0.030@ | 0.056 | 0.093 |
| G614 | 30.0 ×# | 0.116 | 0.064 | 0.250 |
| G614 | 15.0 × | 0.221 | 0.055 | 0.411 |
| G614 | 9.9 × | 0.403 | 0.054 | 0.798 |
| G614 | 7.5 × | 0.598 | 0.046 | 1.061 |
| G614 | 6.0 × | 0.821 | 0.045 | 1.282 |
| G614 | 5.0 × | 1.022 | 0.040 | 1.656 |
| G614 | 4.3 × | 1.445 | 0.042 | 1.889 |

@: Absorbance at 492 nm.
: Samples were diluted with recalcified human serum, which is non-reactive for HBV, HCV and HIV.

The data in Table 8 demonstrate that when the EN-80-2 protein (i.e., core-envelope fusion protein) of HCV and an HIV envelope protein were combined, the absorbance at 492 nm for anti-HCV positive samples showed a synergistic effect, not merely an additive effect. Thus, cooperative interaction between the EN-80-2 protein of HCV and the HIV envelope protein were found.

IV. Fourth Assay

This assay was conducted as set forth in the First Assay, above, and included the provision in a single well of a core-envelope fusion protein of the invention in combination with an HTLV-I envelope protein. The results of the ELISA are set forth in Table 9.

TABLE 9

| Samples | | EN-80-2 | HTLV-I envelope | EN-80-2 + HTLV-I envelope |
|---|---|---|---|---|
| Recalcified human serum | | 0.030@ | 0.035 | 0.084 |
| G614 | 30.0 ×# | 0.116 | 0.031 | 0.375 |
| G614 | 15.0 × | 0.221 | 0.027 | 0.561 |
| G614 | 9.9 × | 0.403 | 0.034 | 1.017 |
| G614 | 7.5 × | 0.598 | 0.033 | 1.303 |
| G614 | 6.0 × | 0.821 | 0.025 | 1.502 |

TABLE 9-continued

| Samples | | EN-80-2 | HTLV-I envelope | EN-80-2 + HTLV-I envelope |
|---|---|---|---|---|
| G614 | 5.0 × | 1.022 | 0.017 | >2.0 |
| G614 | 4.3 × | 1.445 | 0.021 | >2.0 |

@: Absorbance at 492 nm.
: Samples were diluted with recalcified human serum which is non-reactive for HBV, HCV and HIV.

The data in Table 9 demonstrate that when the EN-80-2 protein of HCV and an HTLV-I envelope protein were combined, the absorbance at 492 nm for anti-HCV samples showed a synergistic effect, not merely an additive effect. Thus, cooperative interactions between the EN-80-2 protein of HCV and the HTLV-I envelope protein were found.

V. Fifth Assay

This assay was conducted as set forth in the First Assay, above, and included the provision in a single well of a core-envelope fusion protein of the invention in combination with an HTLV-I pol protein. The results of the ELISA are set forth in Table 9.

TABLE 10

| Samples | | EN-80-2 | HTLV-I pol& | EN-80-2 + HTLV-I pol |
|---|---|---|---|---|
| Recalcified human serum | | 0.027@ | 0.039 | 0.073 |
| G614 | 15.0 × | 0.167 | 0.057 | 0.379 |
| G614 | 9.9 × | 0.288 | 0.047 | 0.543 |
| G614 | 7.5 × | 0.418 | 0.060 | 0.805 |
| G614 | 6.0 × | 0.600 | 0.053 | 1.188 |
| G614 | 5.0 × | 0.706 | 0.040 | 1.568 |
| G614 | 4.3 × | 0.867 | 0.047 | 1.644 |
| 8-5 | | 0.436 | 0.052 | 0.779 |

&: The approximate molecular weight of HTLV-I pol protein is 16,000 daltons.
@: Absorbance at 492 nm.
: Samples were diluted with recalcified human serum, which is non-reactive for HBV, HCV and HIV.

The data in Table 10 demonstrate that when the EN-80-2 protein of HCV and an HTLV-I pol protein were combined, the absorbance at 492 nm for anti-HCV samples showed a synergistic effect, not merely an additive effect. Thus, cooperative interactions between the EN-80-2 protein of HCV and the HTLV-I pol protein were found.

VI. Sixth Assay

This assay shows the results of an ELISA performed according to the protocol set forth in the First Assay, above, wherein a partial core protein was combined with the EN-80-1 (NS5) protein of HCV. The partial core protein consisted of amino acids 1 through 120, and was a gift from the Development Center of Biotechnology (DCB) in Taiwan.

Sample source I: G235 was a GPT abnormal sample, which was anti-HCV antibody negative and was collected from the Taipei blood donation center.

Sample source II: G614 and G615 were anti-HCV positive samples and were purchased from the U.S.A.

TABLE 11

| Sample | EN-80-1 | partial core | EN-80-1 + partial core |
|---|---|---|---|
| G235 | 0.002@ | 0.082 | 0.078 |
| G614 | 0.004 | 1.142 | 1.243 |
| 6615 | 0.000 | 1.332 | 1.430 |

@: Absorbance at 492 nm.

The data in Table 11 demonstrate that when the partial core (amino acids 1 through 120) and EN-80-1 proteins were coated together, the absorbance at 492 nm of anti-HCV positive samples was not synergistic. No cooperative interaction between partial core and NS5 proteins of HCV were found.

VII. Seventh Assay

Table 12 depicts the results of an assay that was similar to that in the Fifth Assay (V), and shows that there were no cooperative interactions between the HBV antigens HBsAg and HBcAg and the EN-80-1 protein of HCV.

HBsAg: purified from HBsAg positive human plasma.
HBcAg: derived from FBV cDNA fragment.
Sample source I: G30 and G49 were GPT abnormal samples, which were anti-HCV antibody positive and were collected fro the Taipei Blood Donation Center.
Sample source II: G612, G613, G614 and G615 were anti-HCV antibody positive and were purchased from the United States of America.

TABLE 12

| Sample | | EN-80-1 | HBsAg | HBcAg | EN-80-1 + HBsAg | EN-80-1 + HBcAg |
|---|---|---|---|---|---|---|
| G30 | 102X@ | 0.088# | 0.117 | 0.162 | 0.186 | 0.219 |
| G49 | 42X | 0.063 | 0.125 | 0.174 | 0.146 | 0.190 |
| G612 | 804X | 0.096 | 0.111 | 0.145 | 0.178 | 0.187 |
| G613 | 52X | 0.195 | 0.165 | 0.137 | 0.232 | 0.239 |
| G614 | 16X | 0.059 | 0.124 | 0.123 | 0.111 | 0.116 |
| G615 | 16X | 0.053 | 0.107 | 0.134 | 0.158 | 0.232 |

@Samples were serially diluted with recalcified human serum, which was non-reactive for HBV, HCV, and HIV.
Absorbance at 492 nm.

The data in Table 12 demonstrate that when the HBsAg or the HBcAg were coated together with the EN-80-1 (NS5) protein, the absorbance of anti-HCV positive samples was not synergistic. No apparent interactions between the HBsAg and the EN-80-1 protein, or the HBcAg and the EN-80-1 protein, were found.

VIII. Eighth Assay

Table 13 shows a comparison of the detection of anti-HCV antibodies between the EverNew Anti-HCV EIA and the Abbott's kit (II). The samples for the test were obtained from the following sources:

Sample source I: G23, G26, G30, G32, G49, G58, G114, G128, G186, G231, G250 and G262 were GPT abnormal samples, which were anti-HCV antibody positive and were collected from Taipei blood donation center.

Sample source II: G612, G613, G614 and G615 were anti-HCV antibody positive and were purchased from U.S.A.

Sample source III: VGH7, VGH11, VGH12, VGH13, VGH16, VGH26, VGH27, VGH29, VGH30, VGH32, VGH33, VGH40, VGH43, VGH46 and VGH52 were anti-HCV antibody positive and were collected from Taipei Veteran General Hospital.

Classification for the samples from source III:

| | |
|---|---|
| VGH7 | IHD stones |
| VGH11 | NANB, sporadic |
| VGH12 | NANB, sporadic |
| VGH13 | NANB, PTH |
| VGH16 | HCC |
| VGH26 | Liver cirrhosis |
| VGH27 | NANB, sporadic |
| VGH29 | IHD stone |
| VGH30 | Schistosomiasis of liver |
| VGH32 | NANB, sporadic |
| VGH33 | Liver cirrhosis |
| VGH40 | No data |
| VGH43 | NANB, sporadic |
| VGH46 | Liver cirrhosis with HCC |
| VGH52 | NANB, sporadic |

Control: Recalcified human serum (non-reactive with HBV, anti-HCV and HIV). This human serum was also used to dilute the above-mentioned anti-HCV positive samples.

Tested Kits:
  EverNew Anti-HCV EIA—Microtiter wells coated with EN-80-1 antigen.
  EverNew Anti-HCV EIA—Microtiter wells coated with EN-80-2 antigen.
  EverNew Anti-HCV EIA—Microtiter wells coated with EN-80-1 and EN-80-2 antigens.

Reference Kit: Abbott's kit (II).

Results:

TABLE 13

| Sample | Dilution | EN-80-1 | EN-80-2 | EN-80-1 + BN-80-2 | ABBOTT |
|---|---|---|---|---|---|
| Recalcified human serum (Control) | n/a | negative | negative | negative | negative |
| G23 | 20X[@] | negative[$] | positive[#] | positive | positive |
|  | 40X | negative | negative | positive | positive |
| G26 | 8X | negative | positive | positive | positive |
|  | 16X | negative | negative | positive | positive |
| G30 | 51X | negative | negative | positive | positive |
|  | 102X | negative | negative | positive | positive |
| G32 | 51X | positive | negative | positive | positive |
|  | 102X | negative | negative | positive | positive |
| G49 | 21X | negative | negative | positive | positive |
|  | 42X | negative | negative | positive | positive |
| G58 | 16X | negative | positive | positive | positive |
|  | 32X | negative | negative | positive | positive |
| G114 | 10X | negative | positive | positive | positive |
|  | 20X | negative | negative | positive | positive |
| G128 | 120X | negative | negative | positive | positive |
|  | 240X | negative | negative | positive | negative |
| G186 | 42X | negative | negative | positive | positive |
|  | 84X | negative | negative | negative | negative |
| G231 | 336X | negative | negative | positive | positive |
|  | 672X | negative | negative | positive | negative |
| G250 | 168X | negative | negative | positive | positive |
|  | 336X | negative | negative | positive | positive |
| G262 | 84X | negative | positive | positive | positive |
|  | 168X | negative | negative | positive | positive |
| G612 | 402X | negative | negative | positive | positive |
|  | 804X | negative | negative | positive | negative |
| G613 | 26X | negative | negative | positive | positive |
|  | 52X | negative | negative | positive | positive |
| G614 | 8X | negative | positive | positive | positive |
|  | 16X | negative | negative | positive | positive |
| G615 | 8X | negative | positive | positive | positive |
|  | 16X | negative | negative | positive | positive |
| VGH7 | 42X | negative | positive | positive | positive |
|  | 84X | negative | negative | positive | positive |

TABLE 13-continued

| Sample | Dilution | EN-80-1 | EN-80-2 | EN-80-1 + BN-80-2 | ABBOTT |
|---|---|---|---|---|---|
| VGH11 | 126X | positive | negative | positive | positive |
|  | 252X | negative | negative | positive | positive |
| VGH12 | 252X | negative | negative | positive | positive |
|  | 504X | negative | negative | positive | positive |
| VGH13 | 252X | negative | positive | positive | positive |
|  | 504X | negative | negative | positive | positive |
| VGH16 | 252X | negative | negative | positive | positive |
|  | 504X | negative | negative | positive | positive |
| VGH26 | 84X | negative | negative | positive | positive |
|  | 168X | negative | negative | positive | positive |
| VGH27 | 42X | negative | negative | positive | negative |
|  | 84X | negative | negative | positive | negative |
| VGH29 | 42X | negative | positive | positive | positive |
|  | 84X | negative | negative | positive | negative |
| VGH30 | 42X | positive | negative | positive | positive |
|  | 84X | negative | negative | positive | negative |
| VGH32 | 504X | negative | negative | positive | negative |
|  | 1008X | negative | negative | positive | negative |
| VGH33 | 84X | negative | positive | positive | negative |
|  | 168X | negative | negative | positive | negative |
| VGH40 | 9X | negative | negative | positive | negative |
|  | 18X | N.D.[&] | N.D. | negative | negative |
| VGH43 | 9X | negative | negative | positive | negative |
|  | 18X | N.D. | N.D. | positive | negative |
| VGH46 | 9X | negative | negative | positive | positive |
|  | 12X | N.D. | N.D. | positive | positive |
| VGH52 | 126X | negative | negative | positive | positive |
|  | 252X | negative | negative | negative | negative |

[@]Samples were serially diluted with recalcified human serum which was non-reactive with HBV, anti-HCV and HIV.
[$]negative—non-reactive with anti-HCV antibody.
[#]positive—reactive with anti-HCV antibody.
[&]N.D.—not done.

The data in Table 13 in bold show instances of synergy between the core antigen-envelope protein and the nonstructural (NS5) region of HCV. The data in bold also demonstrate instances where the invention provided better detection than the reference Abbott's kit (II) HCV detection kit. These data indicate that the detectability of the microtiter wells coated with EN-80-1 and EN-80-2 antigens was more efficient than the microtiter wells coated with either EN-80-1 antigen or EN-80-2 antigen alone. Furthermore, anti-HCV antibody in samples G128 240X, G231 672X, G612 804X, VGH27 42X, VGH27 84X, VGH29 84X, VGH30 84X, VGH32 504X, VGH32 1008X, VGH33 84X, VGH33 168X, VGH40 9X, VGH43 9X and VGH43 18X could be detected by using EverNew Anti-HCV EIA (microtiter wells coated with EN-80-1 and EN-80-2 antigens) but was not detected using the Abbott's kit (II).

THE PRODUCTION OF MONOCLONAL ANTIBODIES TO THE CORE-LIKE ANTIGEN-ADJACENT PROTEIN

14. Preparation of Antibodies Against HCV

Antibodies against unprocessed core antigen-envelope protein and the NS5 nonstructural protein were produced according to a standard procedure for producing monoclonal antibodies. In particular, a BALB/c mouse was immunized with the purified proteins described above in Examples 2 and 10 mixed with an adjuvant; and then the spleen cells were fused with mouse myeloma cells (FO cells line) using polyethylene glycol to form hybridoma cells. The desired clones producing desired monoclonal antibodies was obtained by screening the titer of the antibodies produced by the hybridoma clones so prepared. In one embodiment of the invention, a hybridoma clone was designated EN-80-1-99.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An assay for indirectly determining the presence of a positive-stranded RNA virus in a sample by detecting antibodies directed thereto, comprising:

a) providing an isolated polypeptide comprising a positive-stranded RNA virus core-like antigen protein joined to an adjacent protein of said positive-stranded RNA virus in unprocessed form, wherein said adjacent protein is sized such that said polypeptide has an epitopic configuration corresponding to an unprocessed core-like antigen-adjacent protein of said positive-stranded RNA virus, b) contacting said isolated polypeptide with said sample under conditions suitable and for a time sufficient for said polypeptide to bind to one or more antibodies reactive with said epitopic configuration corresponding to the unprocessed core-like antigen-adjacent protein and specific for said positive-stranded RNA virus present in said sample, to provide an antibody-bound polypeptide, and c) detecting said antibody-bound polypeptide, and therefrom indirectly determining that said sample contains positive-strianded RNA virus by the detection of antibodies directed to the positive-stranded RNA virus.

2. The assay of claim 1 further comprising, a) in step a), providing a second protein to increase the antigenicity of said isolated polypeptide, b) in step b), contacting said second protein with said sample under conditions suitable and for a time sufficient for said second protein to interact with said isolated polypeptide, and c) in step c), detecting bound antibodies, and therefrom determining that said sample contains said positive-stranded RNA virus.

3. The assay of claim 1 or 2 further comprising the step of binding said isolated polypeptide or said second protein to a solid substrate.

4. The assay of claim 1 or 2 wherein said sample is an unpurified sample.

5. The assay of claim 1 or 2 further comprising, prior to said contacting, the step of obtaining said sample from an animal.

6. The assay of claim 5 wherein said animal is a human being.

7. The assay of claim 1 or 2 wherein said assay is selected from the group consisting of a countercurrent immunoelectrophoresis (CIEP) assay, a radioimmunoassay, a radioimmunoprecipitation, an enzyme-linked immunosorbent assay (ELISA), a dot blot assay, an inhibition or competition assay, a sandwich assay, an immunostick (dipstick) assays, a simultaneous assay, an immunochromatographic assay, an immunofiltration assay, a latex bead agglutination assay, an immunofluorescent assay, a biosensor assay, and a low-ight detection assay.

8. The assay of claim 1 or 2 wherein said assay is not a western blot assay.

9. The assay of claim 1 or 2 comprising providing at least one additional isolated polypeptide, comprising a positive-stranded RNA virus core-like antigen protein joined to an adjacent protein of said positive-stranded RNA virus in unprocessed form, wherein said adjacent protein is sized such that said polypeptide has an epitopic configuration corresponding to an unprocessed core-like antigen-adjacent protein of said positive-stranded RNA virus, wherein at least two of which are obtained from different positive-stranded RNA viruses selected from the group consisting of Hepatitis C virus (HCV), Human Immunodeficiency virus (HIV) and Human T-cell Leukemia virus (HTLV), and wherein the step of contacting comprises contacting the isolated polypeptides with said sample under conditions suitable and for a time sufficient for each of said isolated polypeptides to bind to one or more antibodies specific therefor, thereby providing one or more antibody-bound polypeptides.

10. The essay of claim 1 or 2 comprising providing at least two additional isolated polypeptides, each comprising a positive-stranded RNA virus core-like antigen protein joined to an adjacent protein of said positive-stranded RNA virus in unprocessed form, wherein said adjacent protein is sized such that said polypeptide has an epitopic configuration corresponding to an unprocessed core-like antigen-adjacent protein of said positive-stranded RNA virus, wherein at least three of which are from different positive-stranded RNA viruses selected from the group consisting of Hepatitis C virus (HCV), Human Immunodeficiency virus (HIV) and Human T-cell Leukemia virus (HTLV), and wherein the step of contacting comprises contacting the isolated polypeptides with said sample under conditions suitable and for a time sufficient for each of said isolated polypeptides to bind to one or more antibodies specific therefor, thereby providing one or more anitbody-bound polypeptides.

11. A kit for the indirect detection of a positive-stranded RNA virus by detecting antibodies directed thereto, comprising:

a) an isolated polypeptide conmprising a positive-stranded RNA virus core-like antigen protein joined to an adjacent protein of said positive-stranded RNA virus, wherein said adjacent protein is sized such that said polylpepide has an epitopic configuration specific to an uprocessed core-like antigen-adjacent protein of said positive-stranded RNA virus, bound to a solid substrate, and b) means for detecting antibodies bound to said isolated polypeptide.

12. The kit of claim 11 further comprising a second protein capable of cooperatively interacting with said isolated polypeptide to increase the antigenicity of said isolated polypeptide and means for detecting said second protein.

13. The kit of claim 11 or 12 wherein said kit comprises a) at least two of said isolated polypeptides from at least two positive-stranded RNA viruses selected from the group consisting of Hepatitis C virus (HCV), Human Immunodeficiency virus (HIV) and Human T-cell Leukemia virus (HTLV) and b) means for detecting said at least two isolated polypeptides.

14. The kit of claim 11 or 12 wherein said kit comprises a) at least three of said isolated polypeptides from each of Hepatitis C virus (HCV), Human Immunodeficiency virus (HIV) and Human T-cell Leukemia virus (HTLV) and b) means for detecting said at least three isolated polypeptides.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 1:

GGATCCATGA GCACAAATCC TAAACCT                                          27

(2) INFORMATION FOR SEQ ID NO: 2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 2:

GAATTCGGTG TGCATGATCA TGTCCGC                                          27

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO: 3:

GGATCCCGGT GGAGGATGAG AGGGAAATAT CCG                                   33

(2) INFORMATION FOR SEQ ID NO: 4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 4:

GAATTCCCGG ACGTCCTTCG CCCCGTAGCC AAATTT                                36

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 5:

CACCCAGACA GTCGATTTCA G                                                21

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single (D) TOPOLOGY: linear (xi) SEQUENCE DESCRIPTION: SEQ ID NO: 6:

GTATTTGGTG ACTGGGTGCG TC                                                22

(2) INFORMATION FOR SEQ ID NO: 7:

(i) SEQUENCE CHARACTERISTICS:
        (A) LENGTH: 669 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..669

(xi) SEQUENCE DESCRIPTION: SEQ ID NO: 7:

```
ATG AGC ACA AAT CCT AAA CCT CAA AGA AAA ACC AAA CGT AAC ACC AAC        48
Met Ser Thr Asn Pro Lys Pro Gln Arg Lys Thr Lys Arg Asn Thr Asn
 1               5                  10                  15

CGC CGC CCA CAG GAC GTC AAG TTC CCG GGC GGT GGT CAG ATC GTT GGT        96
Arg Arg Pro Gln Asp Val Lys Phe Pro Gly Gly Gly Gln Ile Val Gly
                20                  25                  30

GGA GTT TAC CTG TTG CCG CGC AGG GGC CCC AGG TTG GGT GTG CGC GCG       144
Gly Val Tyr Leu Leu Pro Arg Arg Gly Pro Arg Leu Gly Val Arg Ala
        35                  40                  45

ACT AGG AAG ACT TCC GAG CGG TCG CAA CCT CGT GGA AGG CGA CAA CCT       192
Thr Arg Lys Thr Ser Glu Arg Ser Gln Pro Arg Gly Arg Arg Gln Pro
 50                  55                  60

ATC CCC AAG GCT CGC CGG CCC GAG GGC AGG ACC TGG GCT CAG CCG GGG       240
Ile Pro Lys Ala Arg Arg Pro Glu Gly Arg Thr Trp Ala Gln Pro Gly
 65                  70                  75                  80

TAC CCT TGG CCC CTC TAT GGC AAT GAG GGT CTG GGG TGG GCA GGA TGG       288
Tyr Pro Trp Pro Leu Tyr Gly Asn Glu Gly Leu Gly Trp Ala Gly Trp
                85                  90                  95

CTC CTG TCA CCC CGA GGC TCT CGG CCT AGT TGG GGC CCC ACG GAC CCC       336
Leu Leu Ser Pro Arg Gly Ser Arg Pro Ser Trp Gly Pro Thr Asp Pro
            100                 105                 110

CGG CGT AGG TCG CGT AAT CTG GGT AAG GTC ATC GAT ACC CTC ACA GGT       384
Arg Arg Arg Ser Arg Asn Leu Gly Lys Val Ile Asp Thr Leu Thr Gly
        115                 120                 125

GGC TTC GCC GAC CTC ATG GGG TAC ATT CCG CTC GTC AGC GCC CCA CTA       432
Gly Phe Ala Asp Leu Met Gly Tyr Ile Pro Leu Val Ser Ala Pro Leu
    130                 135                 140

GGA GGC GCT GCC AGG GCC CTG GGC CAT GGC GTC CGG GTT CTG GAG GAC       480
Gly Gly Ala Ala Arg Ala Leu Gly His Gly Val Arg Val Leu Glu Asp
145                 150                 155                 160

GGC GTG AAC TAT GCA ACA GGG AAT CTG CCC GGT TGC TCT TTC TCT ATC       528
Gly Val Asn Tyr Ala Thr Gly Asn Leu Pro Gly Cys Ser Phe Ser Ile
                165                 170                 175

TTC CTC TTA GCT TTG CTG TCT TGT TTG ACC ATC CCA GCT TCC GCT TAC       576
Phe Leu Leu Ala Leu Leu Ser Cys Leu Thr Ile Pro Ala Ser Ala Tyr
            180                 185                 190

GAG GTG CGC AAC GTG TCC GGG ATA TAC CAT GTT ACG AAC GAT TGC TCC       624
Glu Val Arg Asn Val Ser Gly Ile Tyr His Val Thr Asn Asp Cys Ser
        195                 200                 205

AAC TCA AGT ATC GTG TAT GAG GCA GCG GAC ATG ATC ATG CAC ACC           669
Asn Ser Ser Ile Val Tyr Glu Ala Ala Asp Met Ile Met His Thr
    210                 215                 220
```

(2) INFORMATION FOR SEQ ID NO: 8:

(i) SEQUENCE CHARACTERISTICS:
        (A) LENGTH: 223 amino acids
        (B) TYPE: amino acid
        (D) TOPOLOGY: linear (ii) MOLECULE TYPE: protein (xi) SEQUENCE DESCRIPTION: SEQ ID NO: 8:

Met Ser Thr Asn Pro Lys Pro Gln Arg Lys Thr Lys Arg Asn Thr Asn
 1               5                  10                  15

Arg Arg Pro Gln Asp Val Lys Phe Pro Gly Gly Gln Ile Val Gly
            20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
 50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Gly
            115                 120                 125

Gly Phe Ala Asp Leu Met Gly Tyr Ile Pro Leu Val Ser Ala Pro Leu
130                 135                 140

Gly Gly Ala Ala Arg Ala Leu Gly His Gly Val Arg Val Leu Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
            195                 200                 205

Asn Ser Ser Ile Val Tyr Glu Ala Ala Asp Met Ile Met His Thr
210                 215                 220

(2) INFORMATION FOR SEQ ID NO: 9:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 3..803

(xi) SEQUENCE DESCRIPTION: SEQ ID NO: 9:

CG GTG GAG GAT GAG AGG GAA ATA TCC GTT GAG GCG GAG ATC CTG CGT      47
   Val Glu Asp Glu Arg Glu Ile Ser Val Glu Ala Glu Ile Leu Arg
    1               5                  10                  15

TTT TCC AGG AAA TTC CCC CGG GCG ATA CCC ATA TGG GCC CGC CCG GAT     95
Phe Ser Arg Lys Phe Pro Arg Ala Ile Pro Ile Trp Ala Arg Pro Asp
                20                  25                  30

TAC AAT CCA CCA CTG ATA GAG TCC TGG AAG GAC CCG GAC TAT GTC CCC    143
Tyr Asn Pro Pro Leu Ile Glu Ser Trp Lys Asp Pro Asp Tyr Val Pro
            35                  40                  45

-continued

```
CCG GTG GTA CAC GGG TGC CCA TTG CCA CCT GCC AAG ATC CCT CCA ATA      191
Pro Val Val His Gly Cys Pro Leu Pro Pro Ala Lys Ile Pro Pro Ile
         50                  55                  60

CCA CCT CCA CGG AGG AAG AAG ACG GTT GTC CTG ACA GAG TCC GTC TAT      239
Pro Pro Pro Arg Arg Lys Lys Thr Val Val Leu Thr Glu Ser Val Tyr
 65                  70                  75

ACT TCT GCC CTG GCG GAC GTT GCT ACA AAG ACC TTC GGC AGC TCC GAG      287
Thr Ser Ala Leu Ala Asp Val Ala Thr Lys Thr Phe Gly Ser Ser Glu
 80                  85                  90                  95

TCT ACG CCC GTC GAC AGC GGC ACA GCG ACT GGC CTC CCG ATC AAC CTT      335
Ser Thr Pro Val Asp Ser Gly Thr Ala Thr Gly Leu Pro Ile Asn Leu
             100                 105                 110

CTG ACG ACG GCG ACA AAG GGA TCC GAC GTT GAG TCG TAC TCC TCC ATG      383
Leu Thr Thr Ala Thr Lys Gly Ser Asp Val Glu Ser Tyr Ser Ser Met
         115                 120                 125

CCC CCC CTC GAG GGA GAG CCA GGC GAC CCC GAT CTC AGC GAC GGG TCT      431
Pro Pro Leu Glu Gly Glu Pro Gly Asp Pro Asp Leu Ser Asp Gly Ser
 130                 135                 140

TGG TCT ACT GTG AGC GTG GAG GCT AGT GAG GAC GTT GTC TGC TGC TCG      479
Trp Ser Thr Val Ser Val Glu Ala Ser Glu Asp Val Val Cys Cys Ser
     145                 150                 155

ATG TCC TAC ACA TGG ACA GGC GCT TTA ATC ACG CCA TGC GCT GCG GAG      527
Met Ser Tyr Thr Trp Thr Gly Ala Leu Ile Thr Pro Cys Ala Ala Glu
160                 165                 170                 175

GAG AGC AAA CTG CCC ATC AAT GCG TTG AGC TTC TCT TTG TTG CGT CAC      575
Glu Ser Lys Leu Pro Ile Asn Ala Leu Ser Phe Ser Leu Leu Arg His
             180                 185                 190

CAC AAT ATG GTC TAC GCC ACA ACA TCC CGC AGC GCA GAC CAG CCG CAG      623
His Asn Met Val Tyr Ala Thr Thr Ser Arg Ser Ala Asp Gln Pro Gln
         195                 200                 205

AAA AAG GTC ACC TTT GAC AGA CTG CAA GTC CTG GAC GAC CAC TAC CGG      671
Lys Lys Val Thr Phe Asp Arg Leu Gln Val Leu Asp Asp His Tyr Arg
 210                 215                 220

GAC GTA CTC AAG GAG ATG AAG GCG AAG GCG TCT ACA GTT AAG GCT AAA      719
Asp Val Leu Lys Glu Met Lys Ala Lys Ala Ser Thr Val Lys Ala Lys
             225                 230                 235

CTT CTA TCC GTA GAA GAG GCC TGT AAC GTG ACG CCC CCA CAT TCG GCC      767
Leu Leu Ser Val Glu Glu Ala Cys Asn Val Thr Pro Pro His Ser Ala
240                 245                 250                 255

AAA TCC AAA TTT GGC TAC GGG GCG AAG GAC GTC CGG                      803
Lys Ser Lys Phe Gly Tyr Gly Ala Lys Asp Val Arg
             260                 265
```

(2) INFORMATION FOR SEQ ID NO: 10:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO: 10:

```
Val Glu Asp Glu Arg Glu Ile Ser Val Glu Ala Glu Ile Leu Arg Phe
 1                   5                  10                  15

Ser Arg Lys Phe Pro Arg Ala Ile Pro Ile Trp Ala Arg Pro Asp Tyr
             20                  25                  30

Asn Pro Pro Leu Ile Glu Ser Trp Lys Asp Pro Asp Tyr Val Pro Pro
         35                  40                  45

Val Val His Gly Cys Pro Leu Pro Pro Ala Lys Ile Pro Pro Ile Pro
 50                  55                  60
```

-continued

```
Pro Pro Arg Arg Lys Lys Thr Val Val Leu Thr Glu Ser Val Tyr Thr
65                  70                  75                  80

Ser Ala Leu Ala Asp Val Ala Thr Lys Thr Phe Gly Ser Ser Glu Ser
                85                  90                  95

Thr Pro Val Asp Ser Gly Thr Ala Thr Gly Leu Pro Ile Asn Leu Leu
                100                 105                 110

Thr Thr Ala Thr Lys Gly Ser Asp Val Glu Ser Tyr Ser Ser Met Pro
            115                 120                 125

Pro Leu Glu Gly Glu Pro Gly Asp Pro Asp Leu Ser Asp Gly Ser Trp
            130                 135                 140

Ser Thr Val Ser Val Glu Ala Ser Glu Asp Val Val Cys Cys Ser Met
145                 150                 155                 160

Ser Tyr Thr Trp Thr Gly Ala Leu Ile Thr Pro Cys Ala Ala Glu Glu
                165                 170                 175

Ser Lys Leu Pro Ile Asn Ala Leu Ser Phe Ser Leu Leu Arg His His
                180                 185                 190

Asn Met Val Tyr Ala Thr Thr Ser Arg Ser Ala Asp Gln Pro Gln Lys
            195                 200                 205

Lys Val Thr Phe Asp Arg Leu Gln Val Leu Asp Asp His Tyr Arg Asp
        210                 215                 220

Val Leu Lys Glu Met Lys Ala Lys Ala Ser Thr Val Lys Ala Lys Leu
225                 230                 235                 240

Leu Ser Val Glu Glu Ala Cys Asn Val Thr Pro Pro His Ser Ala Lys
                245                 250                 255

Ser Lys Phe Gly Tyr Gly Ala Lys Asp Val Arg
            260                 265
```